US009763965B2

(12) United States Patent
Van Oort et al.

(10) Patent No.: US 9,763,965 B2
(45) Date of Patent: Sep. 19, 2017

(54) AGGREGATE PARTICLES

(71) Applicant: GlaxoSmithKline Intellectual Property Development Limited, Brentford, Middlesex (GB)

(72) Inventors: Michiel Mary Van Oort, Research Triangle Park, NC (US); John N. Hong, Research Triangle Park, NC (US)

(73) Assignee: GlaxoSmithKline Intellectual Property Development Limited, Brentford Middlesex (GB)

( * ) Notice: Subject to any disclaimer, the term of this patent is extended or adjusted under 35 U.S.C. 154(b) by 0 days.

(21) Appl. No.: 14/394,132

(22) PCT Filed: Apr. 11, 2013

(86) PCT No.: PCT/EP2013/057555

§ 371 (c)(1),
(2) Date: Oct. 13, 2014

(87) PCT Pub. No.: WO2013/153146

PCT Pub. Date: Oct. 17, 2013

(65) Prior Publication Data

US 2015/0083127 A1 Mar. 26, 2015

Related U.S. Application Data

(60) Provisional application No. 61/774,698, filed on Mar. 8, 2013, provisional application No. 61/623,672, filed on Apr. 13, 2012.

(51) Int. Cl.

| | |
|---|---|
| *A61K 31/439* | (2006.01) |
| *A61K 31/58* | (2006.01) |

(Continued)

(52) U.S. Cl.

CPC ............ *A61K 31/58* (2013.01); *A61K 9/0075* (2013.01); *A61K 9/145* (2013.01); *A61K 9/1611* (2013.01);

(Continued)

(58) Field of Classification Search

None

See application file for complete search history.

(56) References Cited

U.S. PATENT DOCUMENTS 4,590,206 A 5/1986 Forrester et al.
5,853,698 A 12/1998 Straub et al.

(Continued)

FOREIGN PATENT DOCUMENTS

CN 102247336 B 3/2013
DE 102005028696 A1 12/2006

(Continued)

OTHER PUBLICATIONS

Anonymous; View of NCTO1573624 on Apr. 6, 2012; Retrieved from internet: URL:http:/clinicaltrials.gov/archive/NCTO1573624/2012_04_06;2012; pp. 1-4.

(Continued)

*Primary Examiner* — Robert A Wax
*Assistant Examiner* — Melissa Mercier
(74) *Attorney, Agent, or Firm* — James P. Riek; R. Steve Thomas; William R. Marjarian

(57) ABSTRACT

The present invention relates to aggregate particles comprising nanoparticulate drug particles. In particular, the present invention is directed to aggregate particles comprising nanoparticulate drug particles of umeclidinium bromide and optionally vilanterol trifenatate and/or fluticasone furoate. Aggregate particles of the present invention may further comprise nanoparticulate excipient particles and one or more binders. The invention also relates to powder (Continued)

Typical XRPD Patterns for the Input Drug Substances (Compound A, Compound B and Compound C)

compositions suitable for inhalation that comprise said aggregate particles, processes of producing said aggregate particles, and use of said powder compositions in the treatment of respiratory diseases, such as asthma and COPD.

23 Claims, 16 Drawing Sheets

(51) Int. Cl.
*A61K 9/14* (2006.01)
*A61K 9/16* (2006.01)
*A61K 31/138* (2006.01)
*A61K 9/00* (2006.01)
*A61K 45/06* (2006.01)

(52) U.S. Cl.
CPC .......... *A61K 9/1617* (2013.01); *A61K 9/1623* (2013.01); *A61K 9/1694* (2013.01); *A61K 31/138* (2013.01); *A61K 31/439* (2013.01); *A61K 45/06* (2013.01)

(56) References Cited

U.S. PATENT DOCUMENTS

| | | | |
|---|---|---|---|
| 5,976,574 | A | 11/1999 | Gordon et al. |
| 6,001,336 | A | 12/1999 | Gordon et al. |
| 6,537,983 | B1 | 3/2003 | Biggadike et al. |
| 6,759,398 | B2 | 7/2004 | Biggadike |
| 6,878,698 | B2 | 4/2005 | Biggadike et al. |
| 6,884,794 | B2 | 4/2005 | Staniforth et al. |
| 7,101,866 | B2 | 9/2006 | Biggadike et al. |
| 7,267,813 | B2 | 9/2007 | Watanabe et al. |
| 7,361,787 | B2 | 4/2008 | Box et al. |
| 7,439,393 | B2 | 10/2008 | Box et al. |
| 7,488,827 | B2 | 2/2009 | Laine et al. |
| 7,498,440 | B2 | 3/2009 | Laine et al. |
| 7,629,335 | B2 | 12/2009 | Biggadike et al. |
| 7,736,670 | B2 | 6/2010 | Staniforth et al. |
| 7,776,895 | B2 | 8/2010 | Box et al. |
| 7,982,067 | B2 | 7/2011 | Box et al. |
| 8,048,451 | B2 | 11/2011 | Staniforth et al. |
| 8,182,791 | B2 | 5/2012 | Staniforth et al. |
| 8,183,257 | B2 | 5/2012 | Laine et al. |
| 8,309,572 | B2 | 11/2012 | Laine et al. |
| RE44,874 | E | 4/2014 | Box et al. |
| 2002/0102294 | A1* | 8/2002 | Bosch .................. A61K 9/0075 424/450 |
| 2003/0166509 | A1 | 9/2003 | Edwards et al. |
| 2003/0215517 | A1 | 11/2003 | Grawe et al. |
| 2004/0037785 | A1 | 2/2004 | Staniforth et al. |
| 2004/0071635 | A1 | 4/2004 | Staniforth et al. |
| 2005/0139144 | A1 | 6/2005 | Muller et al. |
| 2005/0191357 | A1 | 9/2005 | Kawashima et al. |
| 2005/0201950 | A1 | 9/2005 | Staniforth et al. |
| 2006/0214037 | A1 | 9/2006 | Holland et al. |
| 2007/0172653 | A1 | 7/2007 | Berkland et al. |
| 2009/0004262 | A1 | 1/2009 | Shaw et al. |
| 2009/0029901 | A1 | 1/2009 | Wood-Kaczmar et al. |
| 2009/0068276 | A1 | 3/2009 | Main et al. |
| 2009/0181100 | A1 | 7/2009 | Bosch et al. |
| 2009/0298742 | A1 | 12/2009 | Roche et al. |
| 2011/0269970 | A1 | 11/2011 | Box et al. |
| 2012/0027863 | A1 | 2/2012 | Staniforth et al. |
| 2012/0309725 | A1 | 12/2012 | Baker et al. |
| 2014/0113888 | A1 | 4/2014 | Crater |
| 2015/0093440 | A1 | 4/2015 | Hong et al. |
| 2015/0313841 | A1 | 11/2015 | Jones et al. |

FOREIGN PATENT DOCUMENTS

| | | | |
|---|---|---|---|
| EP | 1829533 | A2 | 9/2007 |
| EP | 1905432 | A1 | 4/2008 |
| EP | 2050437 | A1 | 4/2009 |
| EP | 2219615 | A2 | 8/2010 |
| EP | 2253306 | A1 | 11/2010 |
| GB | 200029261 | | 11/2000 |
| IN | 2005MU00228 | | 5/2007 |
| JP | 57171918 | A | 10/1982 |
| JP | 11079985 | A2 | 3/1999 |
| JP | 2008007426 | A2 | 1/2008 |
| WO | 9609814 | A1 | 4/1996 |
| WO | 9632149 | A1 | 10/1996 |
| WO | 9741833 | A1 | 11/1997 |
| WO | 9744013 | A1 | 11/1997 |
| WO | 9831346 | A1 | 7/1998 |
| WO | 9835666 | A1 | 8/1998 |
| WO | 9851282 | A1 | 10/1998 |
| WO | 9902665 | A1 | 1/1999 |
| WO | 9916419 | A1 | 4/1999 |
| WO | 0027363 | A1 | 5/2000 |
| WO | 0028979 | A1 | 5/2000 |
| WO | 0053157 | A1 | 9/2000 |
| WO | 0053158 | A1 | 9/2000 |
| WO | 0149263 | A1 | 7/2001 |
| WO | 0178693 | A2 | 10/2001 |
| WO | 0178694 | A2 | 10/2001 |
| WO | 0178695 | A2 | 10/2001 |
| WO | 0228377 | A1 | 10/2001 |
| WO | 0211695 | A2 | 2/2002 |
| WO | 0224169 | A1 | 3/2002 |
| WO | 0243700 | A2 | 6/2002 |
| WO | 0243701 | A2 | 6/2002 |
| WO | 0243702 | A2 | 6/2002 |
| WO | 02074348 | A1 | 9/2002 |
| WO | 03024396 | A2 | 3/2003 |
| WO | 03024439 | A1 | 3/2003 |
| WO | 03039515 | A1 | 5/2003 |
| WO | 03043586 | A2 | 5/2003 |
| WO | 03048666 | A1 | 6/2003 |
| WO | 03077886 | A1 | 9/2003 |
| WO | 03080034 | A2 | 10/2003 |
| WO | 2004110404 | A1 | 12/2004 |
| WO | 2005004845 | A1 | 1/2005 |
| WO | 2005009439 | A1 | 2/2005 |
| WO | 2005018603 | A2 | 3/2005 |
| WO | 2005037280 | A1 | 4/2005 |
| WO | 2005041921 | A2 | 5/2005 |
| WO | 2005046636 | A1 | 5/2005 |
| WO | 2005089717 | A1 | 9/2005 |
| WO | 2005104745 | A2 | 10/2005 |
| WO | 2005105043 | A2 | 11/2005 |
| WO | 2005115462 | A1 | 12/2005 |
| WO | 2005115463 | A1 | 12/2005 |
| WO | 2005115464 | A1 | 12/2005 |
| WO | 2005115465 | A1 | 12/2005 |
| WO | 2005115466 | A1 | 12/2005 |
| WO | 2005115467 | A1 | 12/2005 |
| WO | 2006056812 | A1 | 6/2006 |
| WO | 2006062883 | A2 | 6/2006 |
| WO | 2006062931 | A2 | 6/2006 |
| WO | 2007008851 | A2 | 1/2007 |
| WO | 2007011396 | A2 | 1/2007 |
| WO | 2007012871 | A1 | 2/2007 |
| WO | 2007019229 | A1 | 2/2007 |
| WO | 2007068443 | A1 | 6/2007 |
| WO | 2007068896 | A1 | 6/2007 |
| WO | 2007076295 | A2 | 7/2007 |
| WO | 2007086039 | A1 | 8/2007 |
| WO | 2007106111 | A2 | 9/2007 |
| WO | 2007115033 | A2 | 10/2007 |
| WO | 2008008879 | A2 | 1/2008 |
| WO | 2008012338 | A2 | 1/2008 |
| WO | 2008021142 | A2 | 2/2008 |
| WO | 2008053253 | A2 | 5/2008 |
| WO | 2008058691 | A2 | 5/2008 |
| WO | 2008071742 | A1 | 6/2008 |
| WO | 2008084312 | A2 | 7/2008 |
| WO | 2009036243 | A1 | 3/2009 |
| WO | 2009050217 | A2 | 4/2009 |
| WO | 2009090008 | A1 | 7/2009 |
| WO | 2010009146 | A1 | 1/2010 |
| WO | 2010012419 | A1 | 2/2010 |

(56) References Cited

FOREIGN PATENT DOCUMENTS

| | | | | |
|---|---|---|---|---|
| WO | 2010038086 A2 | | 4/2010 | |
| WO | 2010060529 A1 | | 6/2010 | |
| WO | 2010072354 A1 | | 7/2010 | |
| WO | 2010074113 A1 | | 7/2010 | |
| WO | 2010097114 A1 | | 9/2010 | |
| WO | 2010097115 A1 | | 9/2010 | |
| WO | 2010124198 A2 | | 10/2010 | |
| WO | 2011073002 A1 | | 6/2011 | |
| WO | WO 2011067212 A1 | * | 6/2011 | ........... A61K 31/138 |
| WO | WO-2011067212 A1 | | 6/2011 | |
| WO | 2011120779 A1 | | 10/2011 | |
| WO | 2011131663 A1 | | 10/2011 | |
| WO | 2011160920 A1 | | 12/2011 | |
| WO | 2012041717 A1 | | 4/2012 | |
| WO | 2012051426 A2 | | 4/2012 | |
| WO | 2012168160 A1 | | 12/2012 | |
| WO | 2012168161 A1 | | 12/2012 | |

OTHER PUBLICATIONS

Barnes; "Triple Inhalers for obstructive airways disease: Will they be useful?"; Expert Review of Respiratory Medicine; 2011; vol. 5, No. 3; pp. 297-300.

Laine et al.; "Discovery of Novel 1-Azoniabicyclo[2.2.2] octane Muscarinic Acetylcholine Receptor Antagonists"; Journal of Medicinal Chemistry; 2009; vol. 52, No. 8; pp. 2493-2505.

Aaron et al., Tiotropium in combination with placebo, salmeterol, or fluticasone-salmeterol for treatment of chronic obstructive pulmonary disease: a randomized trial. Ann Intern Med. Apr. 17, 2007;146(8):545-55.

Allen et al., Fluticasone Furoate (FF) A Novel Inhaled Corticosteroid (ICS) Demonstrates Prolonged Lung Absorption Kinetics in Man. American Thoracic Society 2010 International Conference, Abstract D21 Asthma Therapy: New Targets, New Tricks. DOI: http://dx.doi.org/10.1164/ajrccm-conference.2010.181.1_MeetingAbstracts.A5408 (2010).

Broadhead, J., et ai, "Spray Drying of Pharmaceuticals", Drug Development and Industrial Pharmacy, 18(11 &12), 1169-1206(1992).

Biggadike, Fluticasone furoate/fluticasone propionate—different drugs with different properties. Clin Respir J. Jul. 2011;5(3):183-4.

Donohue et al., Efficacy and safety of once-daily umeclidinium/vilanterol 62.5/25 mcg in COPD. Respir Med. Oct. 2013;107(10):1538-46.

Donohue et al., Magnitude of umeclidinium/vilanterol lung function effect depends on monotherapy responses: Results from two randomised controlled trials. Respir Med. Mar. 2016;112:65-74.

Donohue et al., A randomized, double-blind dose-ranging study of the novel LAMA GSK573719 in patients with COPD. Respir Med. Jul. 2012;106(7):970-9.

Kumon, M. et ai, "Can low-dose combination products for inhalation be formulated in single crystalline particles" Eur. J. Pharm. Sci, 40, 16-24 (2010).

Fluticasone, www.Drugs.com, Wolters Kluwer Health (Wayback) (Jun. 4, 2009).

M. Sacchetti, M. Van Oort, Spray Drying and Supercritical Fluid Particle Generation Techniques, "Inhalation Aerosols: Physical and Biological Basis for Therapy", Marcel Dekker, 1996.

GlaxoSmithKline, Evaluate the Safety, Efficacy and Dose Response of GSK573719 in Combination With Fluticasone Furoate in Subjects With Asthma (ILA115938). ClinicalTrials.gov Identifier NCT01573624, First Received Apr. 5, 2012, retrieved online at: https://clinicaltrials.gov/ct2/show/NCT01573624.

Pitchayajittipong et al.; Engineering of Crystalline Combination Inhalation Particles of a Long-Acting beta(2)-Agonist and a Corticosteroid; Pharmaceutical Research; vol. 26, No. 12; pp. 2657-2666 (2009).

Laine et al., The pre-clinical pharmacology of the inhaled muscarinic antagonist G5K573719 predicts once-daily alinical dosing. European Respiratory Journal, 2011; 38(Suppl 55):3450.

File History of U.S. Appl. No. 13/401,890, filed Feb. 22, 2012, Muscarinic Acetylcholine Receptor Antagonists.

File History of U.S. Appl. No. 13/510,962, filed Aug. 20, 2012, Combinations of a Muscarinic Receptor Antagonist and a Beta-2 Adrenoreceptor Agonist.

File History of U.S. Appl. No. 14/970,945, filed Dec. 16, 2015, Combinations of a Muscarinic Receptor Antagonist and a Beta-2 Adrenoreceptor Agonist.

File History of U.S. Appl. No. 14/124,276, filed Jun. 12, 2013, Novel Combination of Therapeutic Agents.

File History of U.S. Appl. No. 14/651,988, filed Dec. 12, 2015, Combination of Umeclidinium, Fluticasone Propionate and Salmeterol Xinafoate for Use in the Treatment of Inflammatory or Respiratory Tract Diseases.

File History of U.S. Appl. No. 13/879,103, filed Oct. 13, 2011 Aggregate Nanoparticulate Edicament Formulations, Manufacture and Use Thereof.

* cited by examiner

Figure 1: Typical XRPD Patterns for the Input Drug Substances (Compound A, Compound B and Compound C)
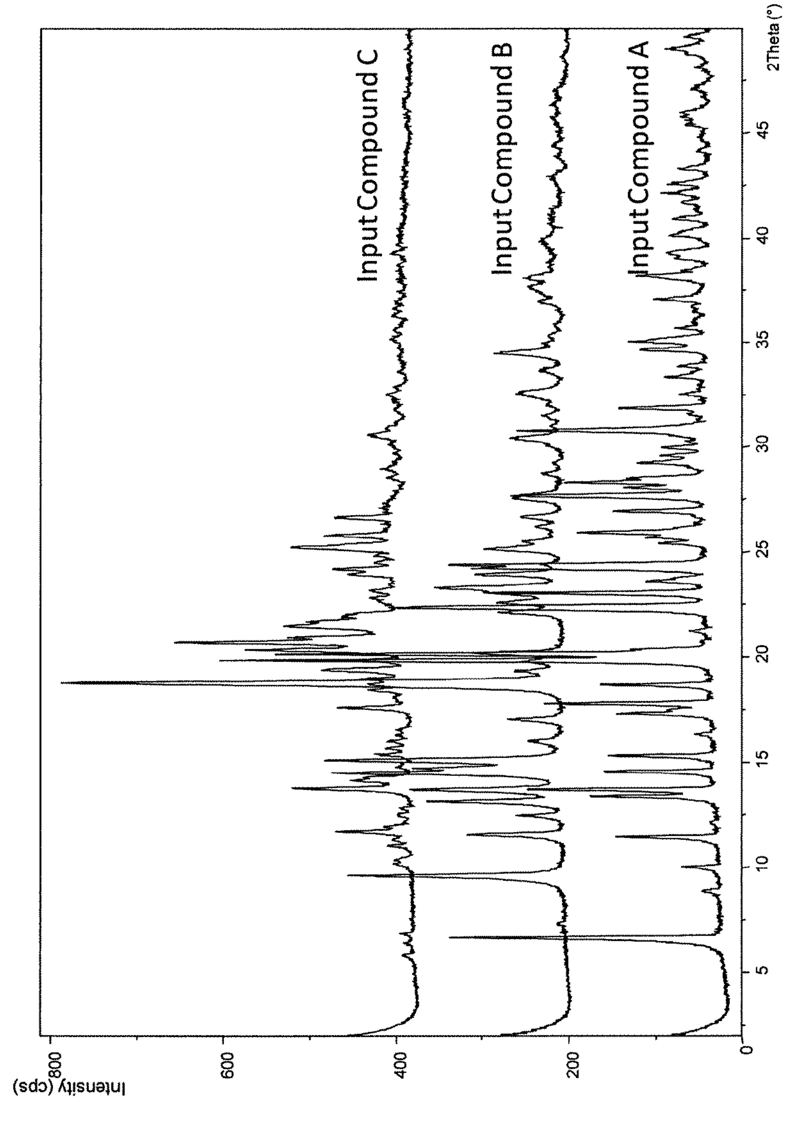

Figure 2: Typical XRPD Patterns for the Input Excipients
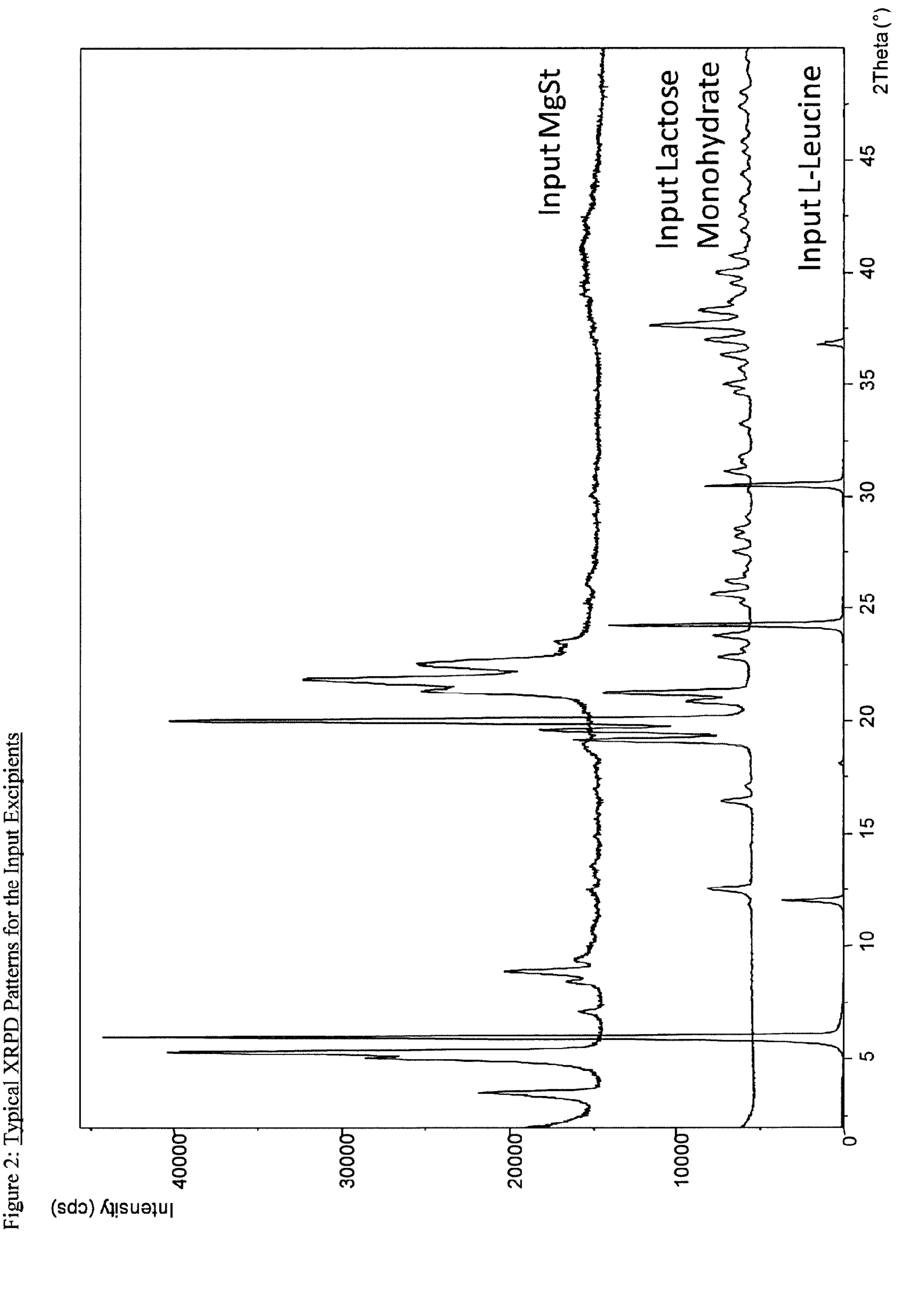

Figure 3: Scanning Electron Micrographs of Aggregate Particles of Sample 1 of Table 1
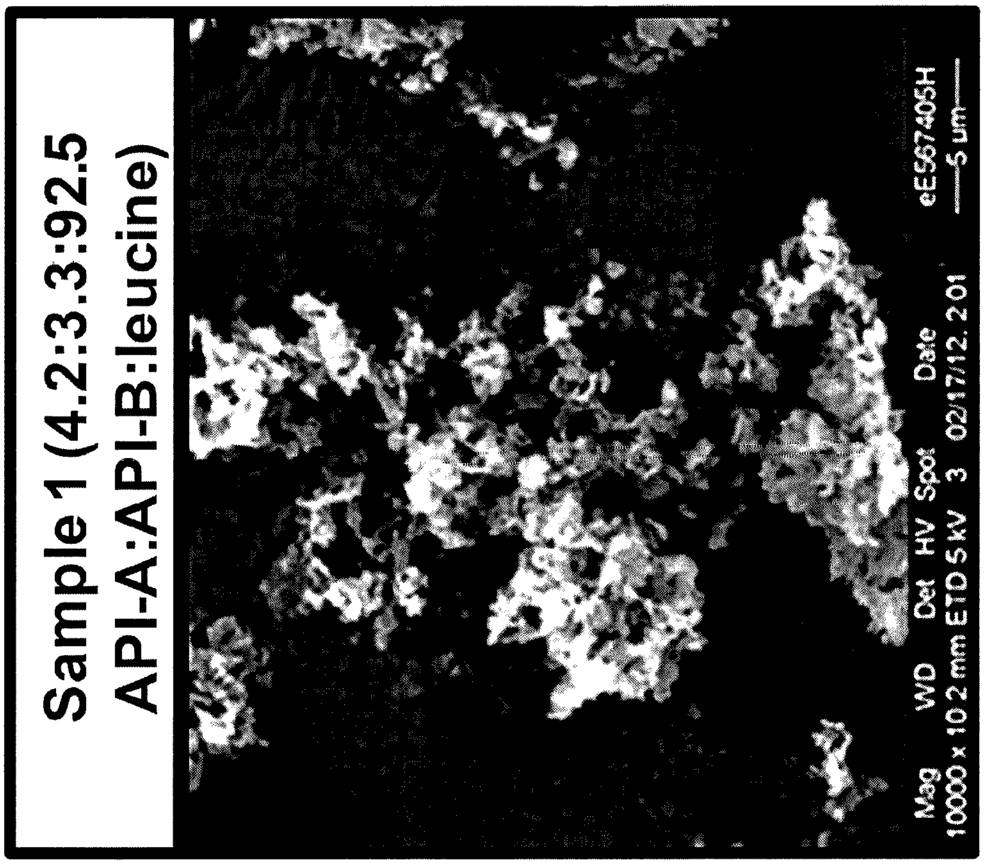

Figure 4: XRPD Patterns for Sample 1 (Spray Dried Powder)
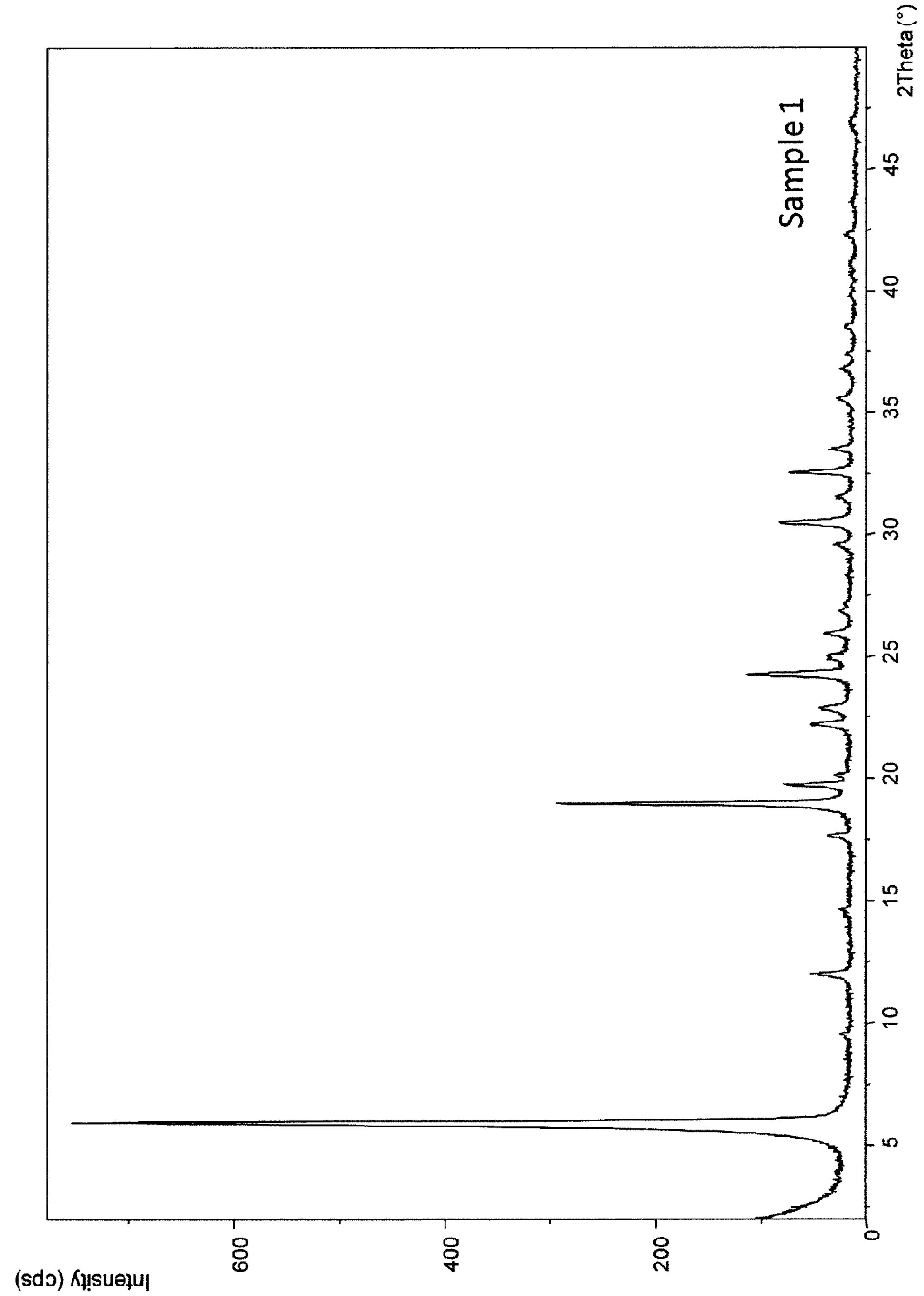

Figure 5: Scanning Electron Micrographs of Aggregate Particles of Samples 2, 3 and 4 of Table 1.
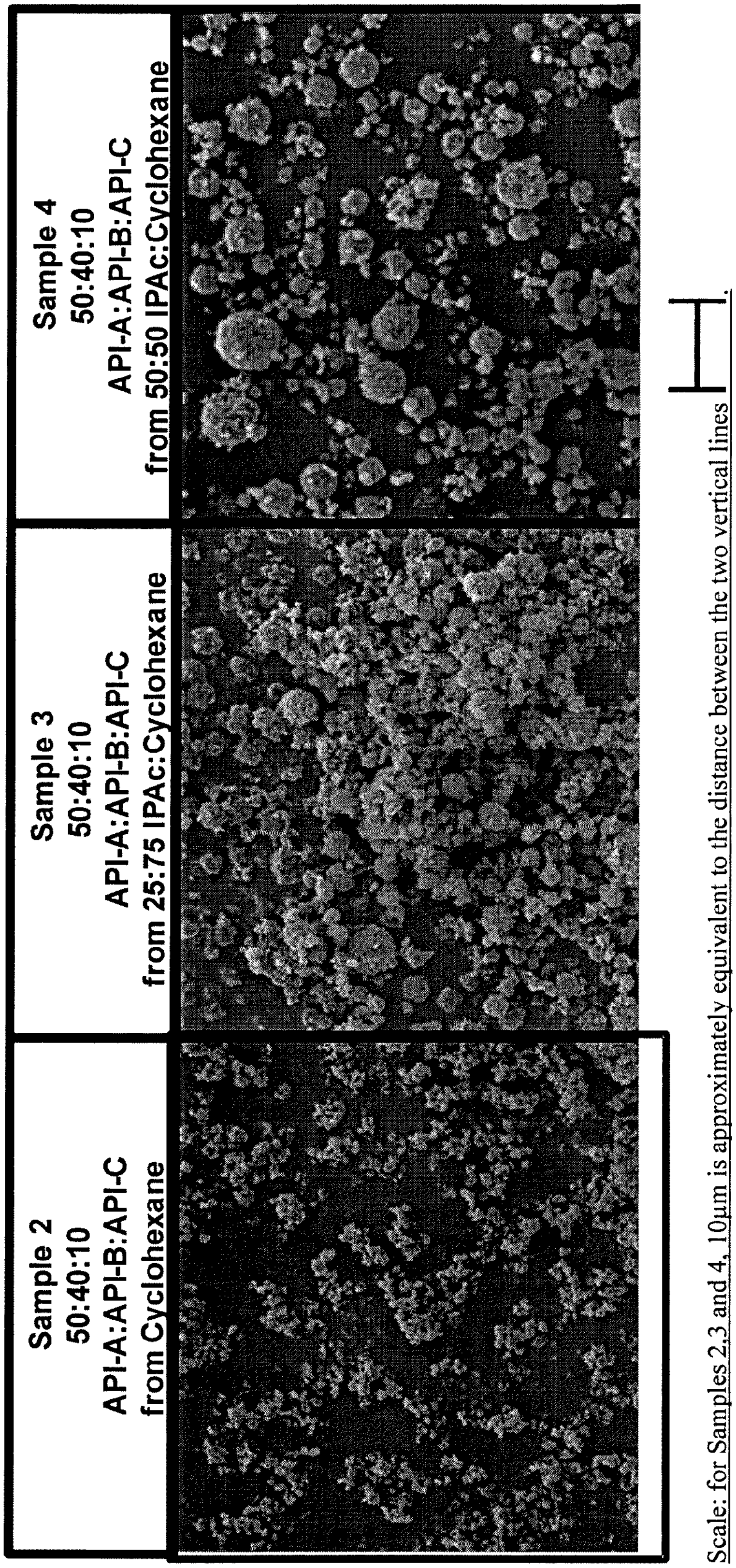
Scale: for Samples 2,3 and 4, 10μm is approximately equivalent to the distance between the two vertical lines.

Figure 6: XRPD Patterns for Samples 2, 3 and 4 (Spray Dried Powder).
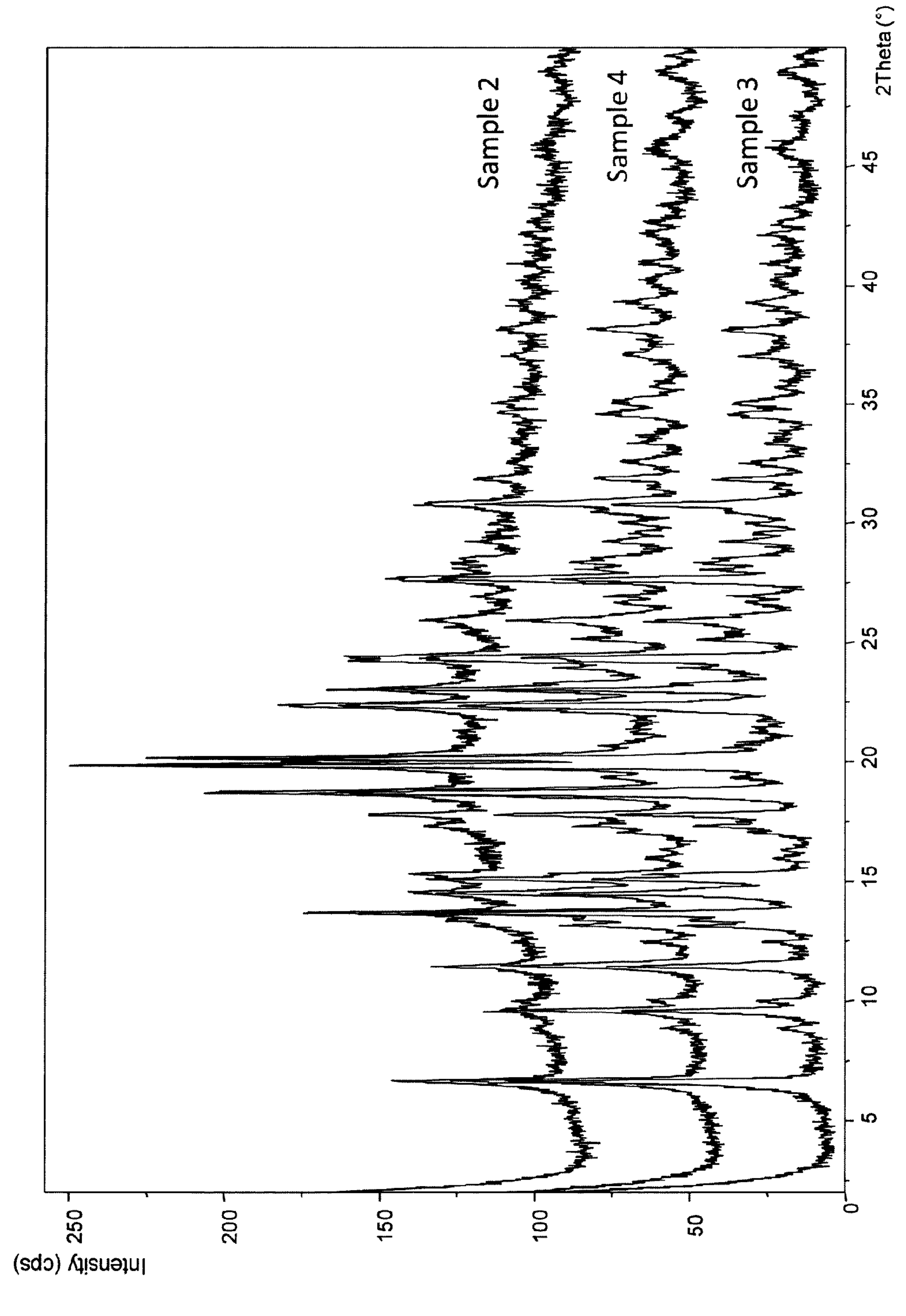

Figure 7: Scanning Electron Micrographs of Aggregate Particles of Samples 5, 6 and 7 of Table 1.
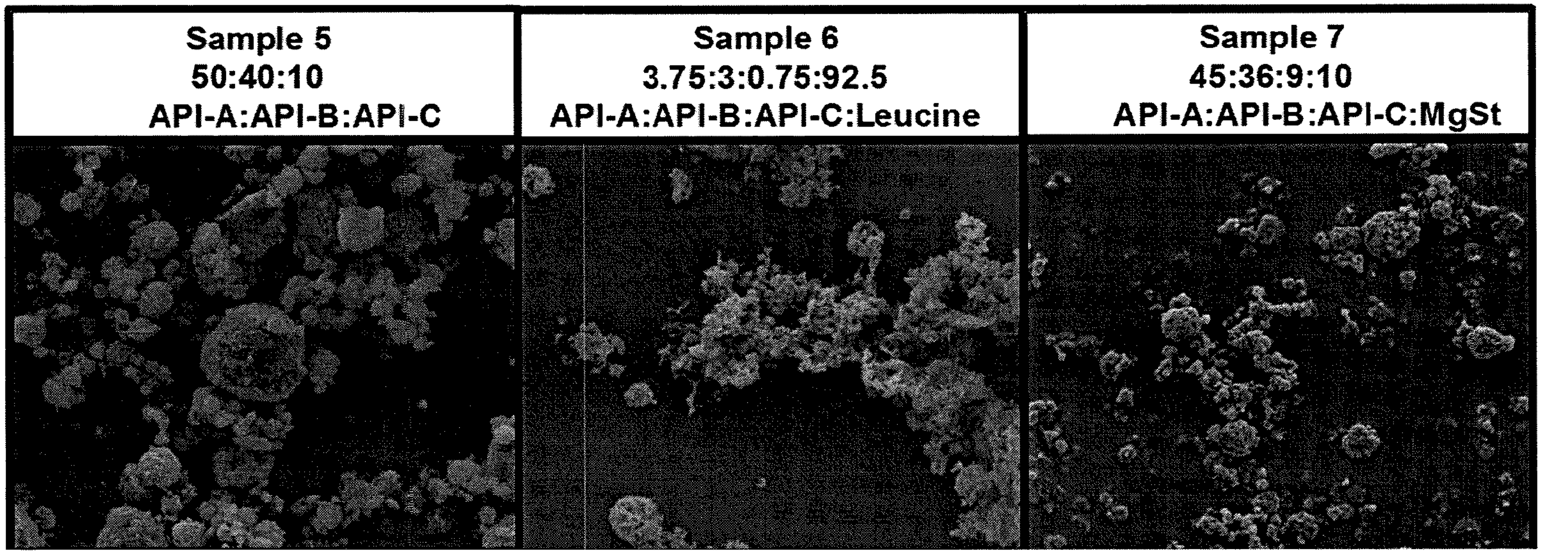
Scale: for Samples 5,6 and 7, 10μm is approximately equivalent to the distance between the two vertical lines 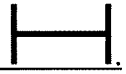.

Figure 8: XRPD Patterns for Samples 5, 6 and 7 (Spray Dried Powder).
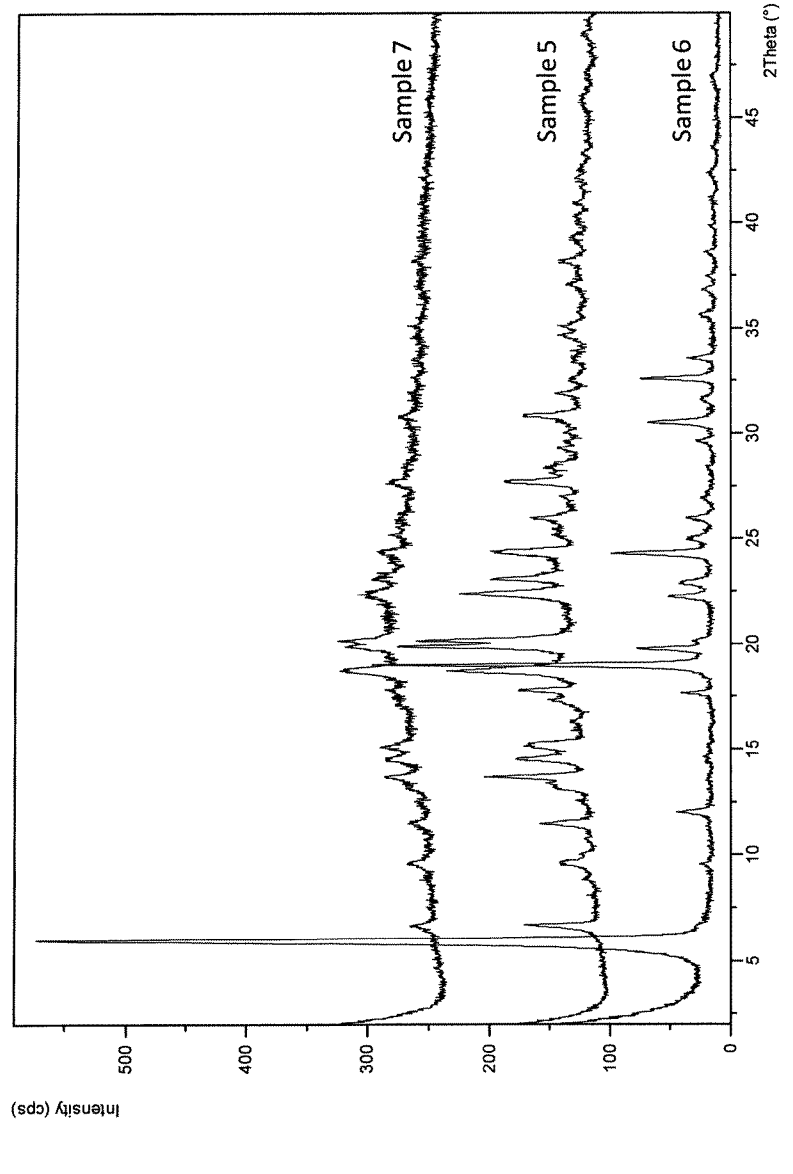

Figure 9: Scanning Electron Micrographs of Aggregate Particles of Samples 8, 9 and 10 of Table 1
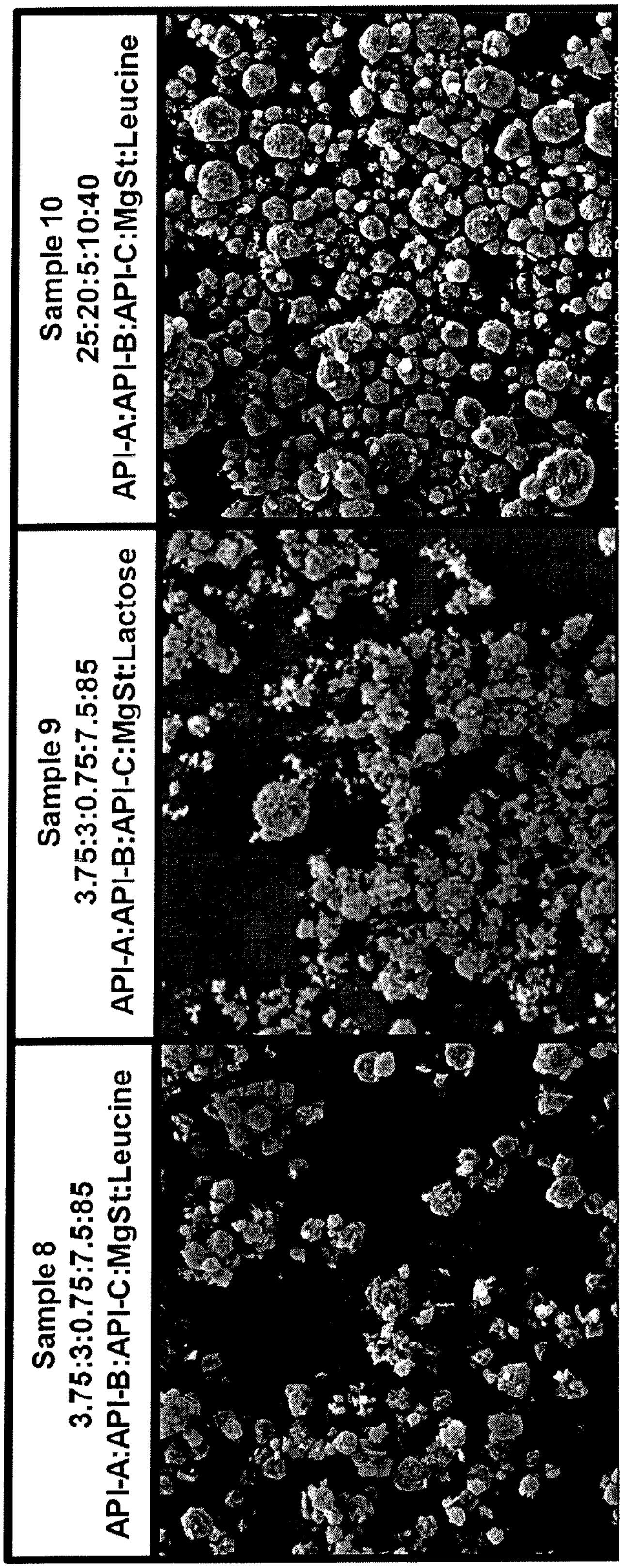
Scale: for Samples 8,9 and 10, 10μm is approximately equivalent to the distance between the two vertical lines.

Figure 10: XRPD Patterns for Samples 8, 9 and 10 (Spray Dried Powder)
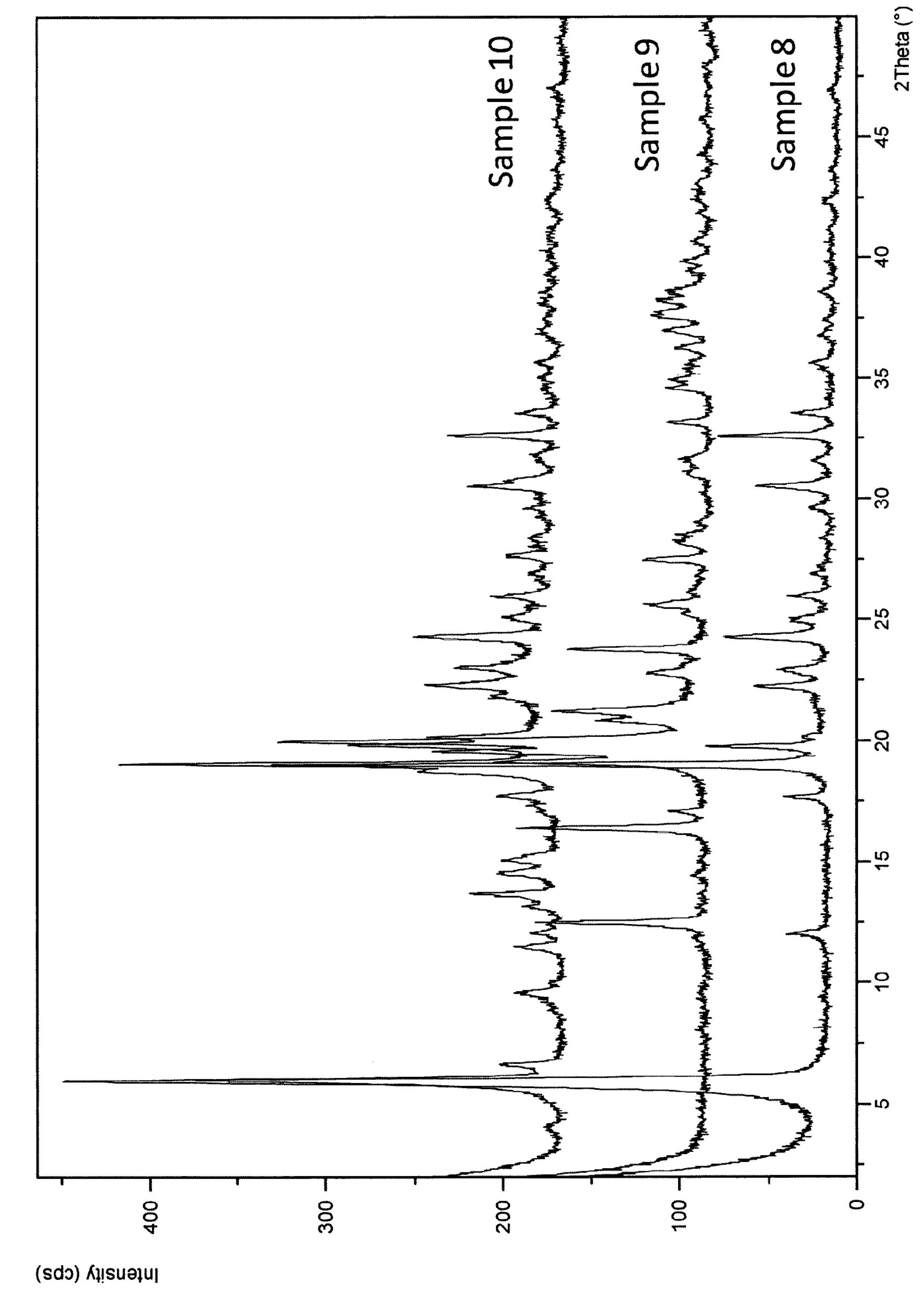

Figure 11: Total Impurities for Samples 5 and 7 Aggregate and Blend Following Stability Storage
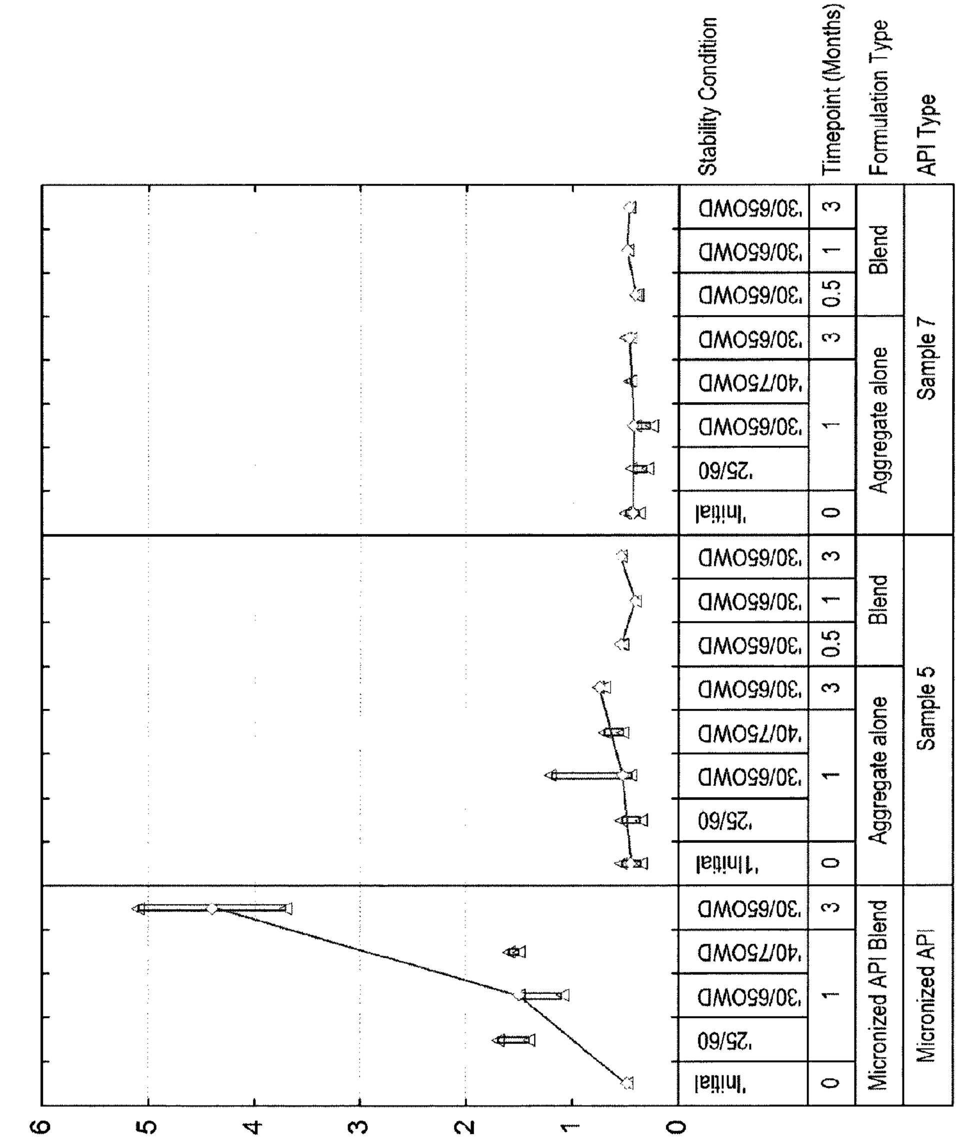
OWD = Overwrap with silica dessicant; 25/60 = 25°C / 60%RH; 30/65 = 30°C / 65%RH; 40/75 = 40°C / 75%RH Figure 12: Percent Fine Particle Dose for Sample 10 Blend Following Stability Storage
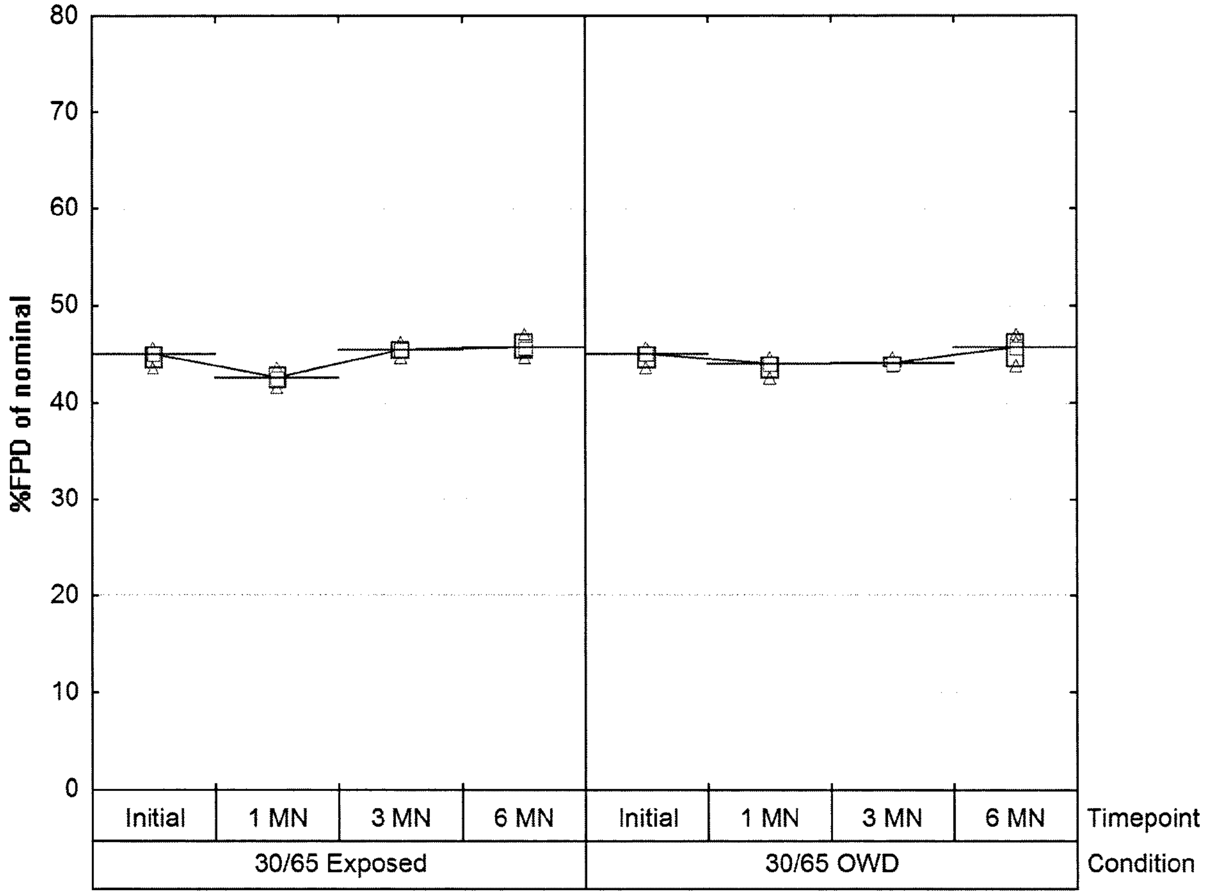
OWD = Overwrap with silica dessicant
30/65 = 30°C / 65%RH Figure 13: Total Impurities for Sample 10 Blend Following Stability Storage
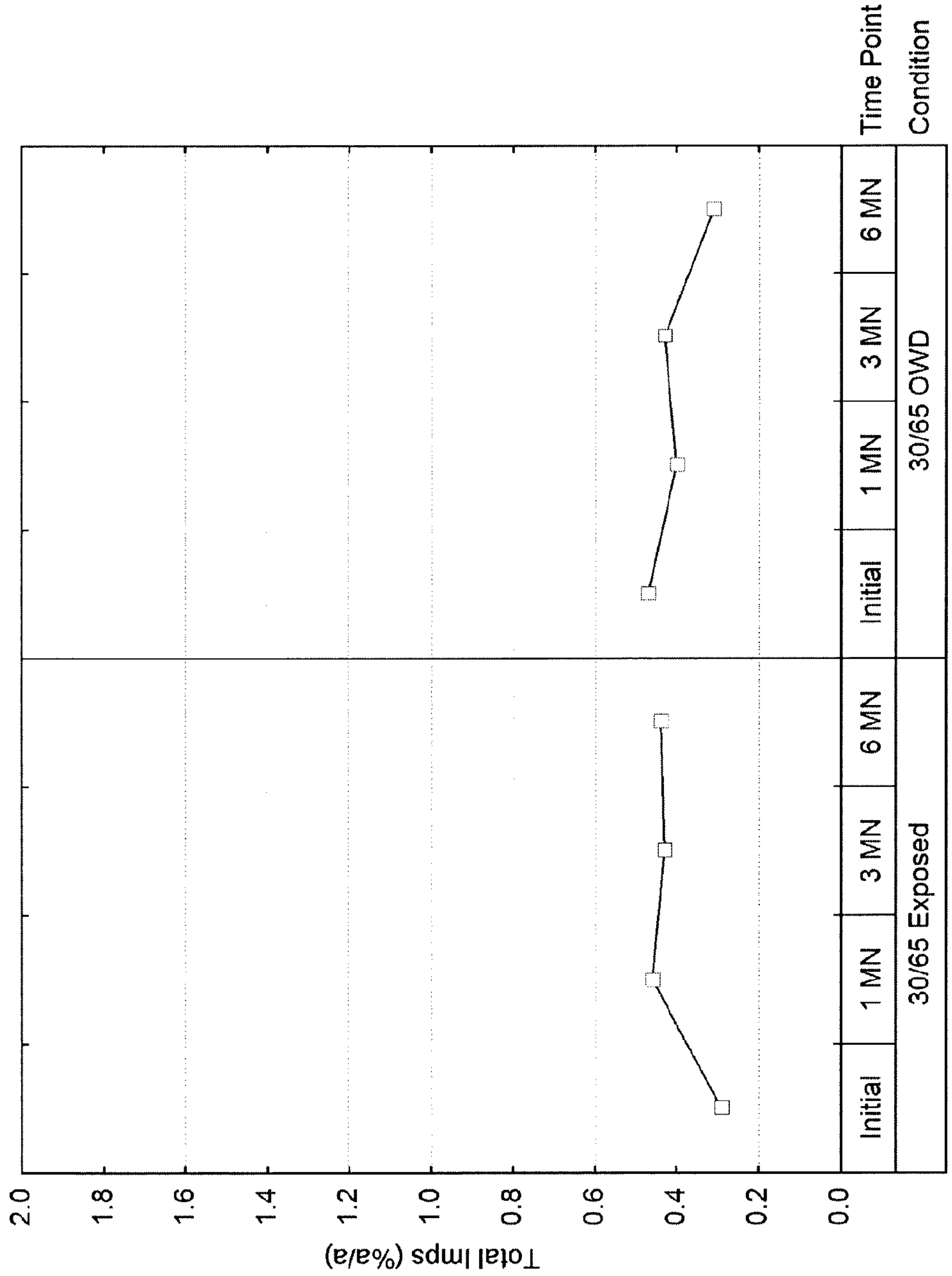
OWD = Overwrap with silica dessicant
30/65 = 30°C / 65%RH Figure 14: Scanning Electron Micrographs of Aggregate Particles of Samples 12, 13 and 14 of Table 12.
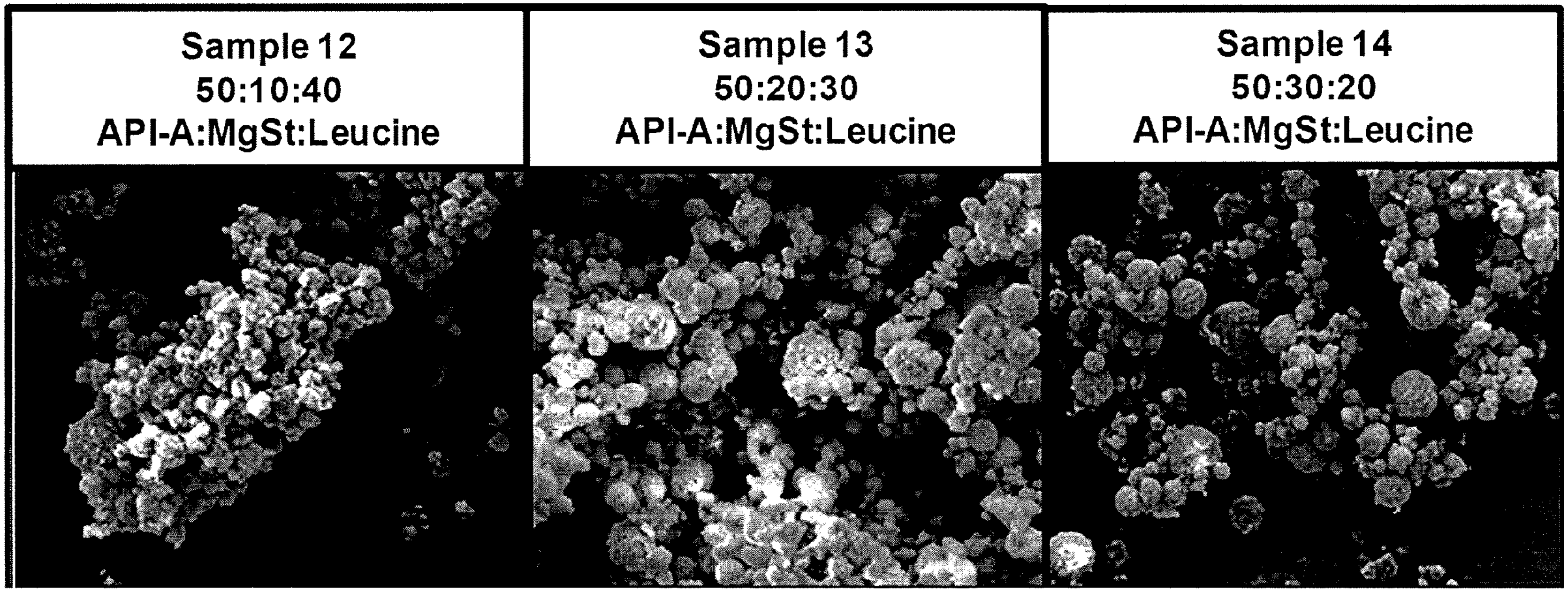
Scale: for Samples 12,13 and 14, 10μm is approximately equivalent to the distance between the two vertical lines 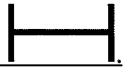.

Figure 15: XRPD Patterns for Samples 12, 13 and 14 (Spray Dried Powder)
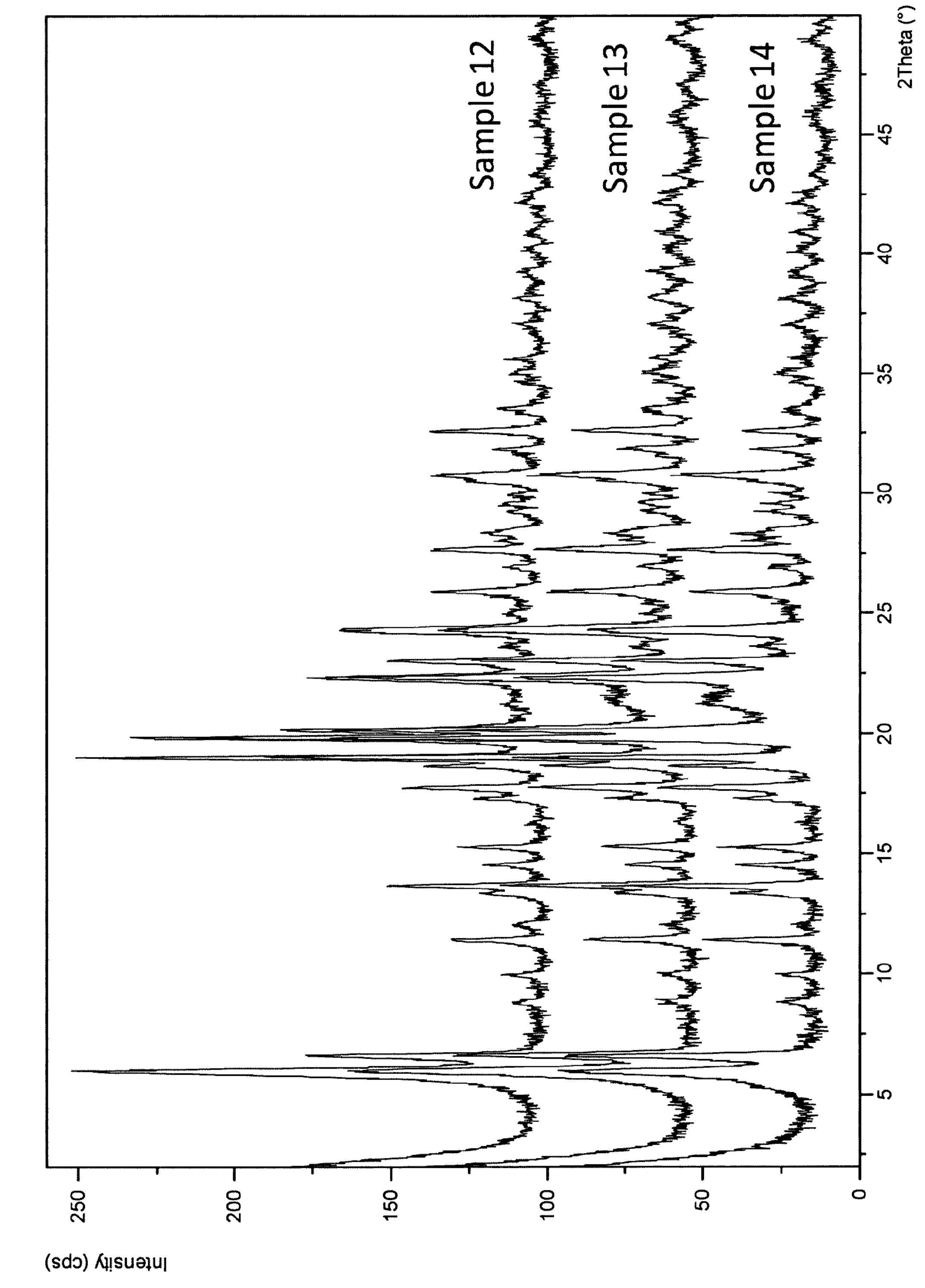

Figure 16: Scanning Electron Micrographs of Aggregate Particle-Lactose Blends of Samples 12, 13 and 14 of Table 15 Following Filling Into Blister Strips
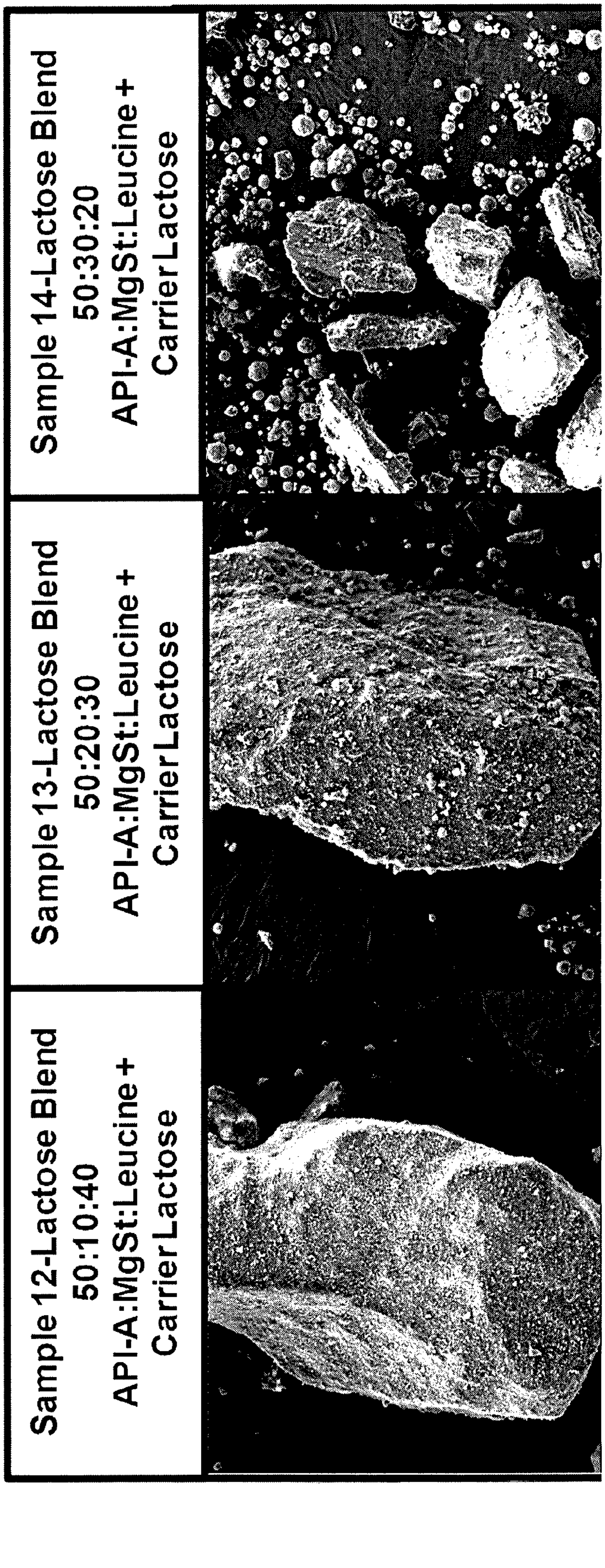
Note: Large irregular particles are of carrier lactose.
Scale: for Samples 12,13 and 14, 20μm is approximately equivalent to the distance between the two vertical lines

AGGREGATE PARTICLES

This application is filed pursuant to 35 U.S.C. §371 as a United States National Phase Application of International Patent Application No. PCT/EP2013/057555 filed Apr. 11, 2013, which claims priority from U.S. Provisional Application No. 61/774,698 filed Mar. 8, 2013 and 61/623,672 filed Apr, 13, 2012.

FIELD OF THE INVENTION

The following invention relates to aggregate particles comprising nanoparticulate drug particles. In particular, the present invention is directed to aggregate particles comprising nanoparticulate drug particles of umeclidinium bromide and optionally vilanterol trifenatate and/or fluticasone furoate. Aggregate particles of the present invention may further comprise nanoparticulate excipient particles and one or more binders. The invention also relates to powder compositions suitable for inhalation that comprise said aggregate particles, processes of producing said aggregate particles, and use of said powder compositions in the treatment of respiratory diseases, such as asthma and COPD.

BACKGROUND OF THE INVENTION

Conventional powder compositions used in DPIs and suspension based MDIs typically contain an active pharmaceutical agent that has been milled to a desired aerodynamic size. In a DPI, the active agent is generally admixed with a coarse carrier/diluent, such as lactose. Other additive materials may be presented to act as physical or chemical stabilizers, dispersants, taste masking agents, etc. In a suspension based MDI, the active agent is suspended in a low-boiling point liquid propellant. The propellant formulation may also include other materials which improve product performance, such as surfactants, etc.

There is a constant effort to improve upon the performance of existing inhalation delivery systems, including the performance of the compositions used in those systems. For example, the desire to improve the current particle based system to provide powders that can be effectively aerosolized to maintain a uniform dose and which can be easily separated from the carrier materials, so as to generate particles of a desired size for targeted site delivery in the pulmonary system, has in recent years, led to a considerable effort to engineer better inhaled particles. One goal of these efforts is the manufacture of particles which are chemically and physically more stable, have greater dispersion, aerosolization and cost efficiencies, so as to optimize inhalation aerosolization and delivery performance.

One alternative approach to size reduction by milling is spray-drying, which has been investigated with some success. Spray drying is a one-step continuous process which can directly produce particles of a desired size range. This approach is amenable to the production of drug powders for inhalation delivery, see, e.g. U.S. Pat. No. 4,590,206, Broadhead, J., et al, "Spray Drying of Pharmaceuticals", Drug Development and Industrial Pharmacy, 18(11&12), 1169-1206 (1992), M. Sacchetti, M. Van Oort, Spray Drying and Supercritical Fluid Particle Generation Techniques, "Inhalation Aerosols: Physical and Biological Basis for Therapy", Marcel Dekker, 1996, and patent publications WO 96/32149, WO 97/41833, WO 97/44013,WO 98/31346 and WO 99/16419.

Particles may be generated from solutions or suspensions. WO 96/09814 describes, for example, the spray drying of budesonide and lactose in ethanol, Published PCT application WO 2001/49263, U.S. Pat. Nos. 6,001,336, 5,976,574 (hydrophobic drugs from organic suspensions), and U.S. Pat. No. 7,267,813 (crystalline inhalable particles comprising a combination of two or more pharmaceutically active compounds) also describe spray dried particles.

While spray drying is suitable for producing respirable sized particles, solid state properties (particularly crystallinity) are difficult to control. The spray drying process, depending on whether solutions or suspensions are being sprayed, and the conditions under which the process occurs, may produce amorphous particles. Such amorphous spray dried particles may have physical and/or chemical stability problems and have an increased tendency to be hygroscopic, all of which are undesirable for pharmaceutical agents. Spray drying solutions having therapeutically active materials with or without excipients therein may produce amorphous material due to the rapid precipitation within the atomized droplets. Moreover, while crystalline materials may be produced, the resulting crystalline product may be of a kinetically preferred form, as opposed to the more thermodynamically stable form. Therefore, an undesirable polymorphic form may result. Further improvement in this area is desirable.

Obtaining crystalline materials reproducibly by spray drying is further complicated when multiple materials are being used, while one of the components may crystallize as desired, another in the same particle may not.

In recent years, attention has turned to nanoparticle drug delivery. Nanoparticles may afford certain advantages in inhaled therapies, particularly their increased rate of dissolution, which is desirable in cases where a pharmaceutically active ingredient is poorly soluble in the environment experienced in the respiratory tract, or where rapid release is desired. Nanoparticles, due to their very small size and large surface area, tend to dissolve rapidly, thus they have been employed for very hydrophobic materials to assist in more rapid dissolution, or where a rapid onset of action is required, such as with immediate release medications.

Pharmaceutically active materials may be delivered as nanoparticles alone, or as nanoparticle components incorporated into larger composite particles which act as delivery vehicles. For example, US 2003-0166509 describes spray drying of nanoparticles to form respirable larger sized particles. The nanoparticles are entrapped in a skeletal framework of precipitated excipient which makes up a larger particle of respirable size. The respirable particles are described as achieving a "sustained action" of drug upon delivery to a target site in the lung, as these composite particles degrade more slowly than a bare nanoparticle and release material in the entrapped nanoparticles as this degradation occurs. Generally, nanoparticles are spray dried from an aqueous suspension. In order to assure the homogeneity of the suspension feed stock, these processes typically include a surfactant in the liquid phase. The use of surfactants, although frequently used, may increase the risk of negative clinical side effects. Thus, removing the surfactant after particle production may be necessary, which increases costs or complexity in manufacturing, if such removal is possible. In spite of this, nanoparticles may be manufactured to be essentially crystalline, which could also avoid the instability and hygroscopicity issues generally found in amorphous particles.

WO 2012/051426 discloses aggregate nanoparticulate medicament formulations, processes of producing said formulations and uses thereof.

The present invention employs spray drying technology, which permits control and efficiency in generating improved aggregate particles, which may provide one or more of the following benefits: increased control of the physical and/or chemical properties of inhaled compositions, particularly crystallinity; increased manufacturing and/or delivery efficiency; greater flexibility in manufacturing, which allows use of a single platform of technology over a variety of pharmaceutically active materials and excipients; an improved drug delivery profile; longer shelf life; providing increased choice to formulators, healthcare providers and/or patients.

SUMMARY OF THE INVENTION

The following invention relates to aggregate particles comprising nanoparticulate drug particles.

In a first aspect, the present invention is directed to aggregate particles comprising nanoparticulate drug particles of umeclidinium bromide.

In a further aspect of the invention, the aggregate particles further comprise nanoparticulate drug particles of vilanterol trifenatate.

In a further aspect of the invention, the aggregate particles further comprise nanoparticulate drug particles of fluticasone furoate.

Aggregate particles of the present invention may further comprise nanoparticulate excipient particles and one or more binders.

The invention further relates to powder compositions suitable for inhalation that comprise said aggregate particles, processes of producing said aggregate particles, and use of said powder compositions in the treatment of respiratory diseases, such as asthma and COPD.

BRIEF DESCRIPTION OF THE FIGURES

FIG. 1 shows typical XRPD patterns for the input drug substances (Compound A, Compound B and Compound C).

FIG. 2 shows typical XRPD patterns for the input excipients prior to bead milling.

FIG. 3 shows Scanning Electron Micrographs of aggregate particles of Sample 1 of Table 1.

FIG. 4 shows XRPD patterns for Sample 1 (spray dried powder).

FIG. 5 shows Scanning Electron Micrographs of aggregate particles of Samples 2, 3, and 4 of Table 1.

FIG. 6 XRPD patterns for Samples 2, 3 and 4 (spray dried powder).

FIG. 7 Scanning Electron Micrographs of aggregate particles of Samples 5, 6 and 7 of Table 1.

FIG. 8 XRPD patterns for Samples 5, 6 and 7 (spray dried powder).

FIG. 9 Scanning Electron Micrographs of aggregate particles of Samples 8, 9 and 10 of Table 1.

FIG. 10 XRPD patterns for Samples 8, 9 and 10 (spray dried powder).

FIG. 11 Total impurities for Samples 5 and 7 aggregate and blend following stability storage.

FIG. 12 Percent fine particle dose for Sample 10 blend following stability storage.

FIG. 13 Total impurities for Sample 10 blend following stability storage.

FIG. 14 Scanning Electron Micrographs of aggregate particles of Samples 12, 13 and 14 of Table 12.

FIG. 15 XRPD patterns for Samples 12, 13 and 14 (spray dried powder).

FIG. 16 Scanning Electron Micrographs of aggregate particle-lactose blends of Samples 12, 13 and 14 of Table 15 following filling into blister strips.

DETAILED DESCRIPTION OF THE INVENTION

The present invention relates to aggregate particles comprising nanoparticulate drug particles of umeclidinium bromide and optionally nanoparticulate excipient particles, and optionally a binder. The invention further relates to powder compositions suitable for inhalation that comprise said aggregate particles, processes of producing said aggregate particles, and use of said powder compositions in the treatment of respiratory diseases, such as asthma and COPD.

The present invention discloses aggregate particles that are prepared by processes employing spray-drying technology. These processes, which are a further aspect of the invention, may provide increased control of the physical and/or chemical properties of inhaled compositions, particularly crystallinity, and increased manufacturing and delivery efficiencies.

The processes described herein may advantageously allow the pre-selected substantially crystalline form of drug and excipient particles to be substantially maintained throughout the process. This negates the risk of preparing powder compositions for inhalation in which the components are in an undesirable crystalline form, which may impact product performance, such as stability (shelf-life).

The aggregate particles of the present invention and powder compositions comprising said particles may provide improved performance over conventional systems, such as improved physical and chemical stability. For example, incorporation of vilanterol trifenatate into aggregate particle constructs with one or more other pharmaceutically active agents or carriers has been shown to significantly improve the chemical stability profile of this beta-agonist, when compared with conventional compositions comprising micronized drug particles and a coarse carrier. They may also possess improved delivery efficiency, such as an increased fine particle dose (%FPD) fraction compared with conventional compositions. In instances where the aggregate particles comprise nanoparticles of more than one drug, there may be less variation in the %FPD between the drugs.

As used herein, the term "%FPD of nominal" means the percentage of the nominal dose that is less than 5 μm.

Incorporation of multiple therapeutically active drugs in the same aggregate particle also ensures that each active is deposited to the same targeted location in the lung tissue, which may provide synergistic effects.

The aggregate particles, being made up of nanoparticles of large surface area, may also possess enhanced dissolution rates compared to conventional compositions comprising micronized drug particles. Incorporating an excipient with relatively high aqueous solubility may further increase the dissolution rate of the aggregate particles. This may improve the pharmacokinetic and safety profile of an inhaled drug compared to micronized drug.

In a first aspect, the present invention is directed to aggregate particles comprising nanoparticulate drug particles of umeclidinium bromide.

As used herein, the term "nanoparticulate" shall mean a particle having a size less than 1 micron, unless otherwise specified or clear from the context in which it is used.

As used herein, the term "drug" means a material having a therapeutic or prophylactic effect in the treatment or prophylaxis of a disease or condition.

In a further aspect of the invention, the aggregate particles further comprise nanoparticulate drug particles of vilanterol trifenatate.

The ratio of umeclidinium to vilanterol may be from about 10:1 to 1:1, for example about 10:1, 5:1, 2.5:1 and 1.25:1. In a further aspect of the invention, the ratio of umeclidinium to vilanterol is 5:1.

In a further aspect of the invention, the aggregate particles further comprise nanoparticulate drug particles of fluticasone furoate.

The ratio of umeclidinium to fluticasone furoate may be from about 1:4 to 2:1, for example about 1:1.6, 1:3. 1.25:1 and 1.25: 2. In a further aspect of the invention, the ratio of umeclidinium to fluticasone furoate is 1.25:1.

As used herein, the term "umeclidinium bromide" means 4-[hydroxy(diphenyl)methyl]-1-{2-[(phenylmethyl)oxy]ethyl}-1-azoniabicyclo[2.2.2]octane bromide.

As used herein, the term "umeclidinium" means 4-[hydroxy(diphenyl)methyl]-1-{2-[(phenylmethyl)oxy]ethyl}-1-azoniabicyclo[2.2.2]octane.

As used herein, the term "fluticasone furoate" means 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

As used herein, the term "vilanterol trifenatate" means 4-{(1R)-2-[(6-{2-[(2,6-dichlorobenzyl)oxy]ethoxy}-hexyl)amino]-1-hydroxyethyl}-2-(hydroxymethyl)phenol triphenylacetate.

As used herein, the term "vilanterol" means 4-{(1R)-2-[(6-{2-[(2,6-dichlorobenzyl)oxy]ethoxy}-hexyl)amino]-1-hydroxyethyl}-2-(hydroxymethyl)phenol.

In one aspect, the present invention provides aggregate particles comprising nanoparticulate drug particles of umeclidinium bromide, vilanterol trifenatate and fluticasone furoate.

In a further aspect, the present invention provides aggregate particles comprising nanoparticulate drug particles of umeclidinium bromide, vilanterol trifenatate and fluticasone furoate, wherein the ratio of umeclidinium to vilanterol is 5:1 and further wherein the ratio of umeclidinium to fluticasone furoate is 1.25:1.

In yet a further aspect of the invention, the nanoparticulate drug particles have a pre-selected substantially crystalline form.

As used herein, the term "pre-selected substantially crystalline form" means the desired crystalline form possessed by a sample of material prior to aggregate particle formation, as determined e.g., by XRPD.

The aggregate particles of the invention may contain nanoparticulate drug particles only, or may further comprise nanoparticulate particles of excipient. One or more excipients may be incorporated into the process for the preparation of aggregate particles. Suitable excipients include, but are not limited to, amino acids, such as leucine, iso-leucine, valine and glycine, sugars, such as lactose, sucrose, glucose, and trehalose, stearates, such as magnesium stearate, sodium stearate, stearic acid and calcium stearate, fatty acid esters, sugar alcohols, such as mannitol, sorbitol, inositol, xylitol, erythritol, lactitol, and malitol, cholesterol, cyclodextrins, EDTA, ascorbic acid, Vitamin E derivatives, di-keto-piperazine, taste masking agents, aspartame, sucralose, and citric acid. Particularly preferred excipients include lactose, leucine, mannitol and magnesium stearate, alone or in combination. In a further aspect of the invention, aggregate particles comprise nanoparticulate excipient particles, and said excipient particles comprise lactose or leucine and magnesium stearate.

In one aspect, the present invention provides aggregate particles comprising nanoparticulate drug particles of umeclidinium bromide, vilanterol trifenatate and fluticasone furoate, and nanoparticulate excipient particles of one or more excipients.

In one aspect, the present invention provides aggregate particles comprising nanoparticulate drug particles of umeclidinium bromide, vilanterol trifenatate and fluticasone furoate, and nanoparticulate excipient particles of leucine and/or magnesium stearate.

In a further aspect, the present invention provides aggregate particles comprising nanoparticulate drug particles of umeclidinium bromide, vilanterol trifenatate and fluticasone furoate, and nanoparticulate excipient particles of one or more excipients, wherein the ratio of umeclidinium to vilanterol is 5:1 and further wherein the ratio of umeclidinium to fluticasone furoate is 1.25:1.

In a further aspect, the present invention provides aggregate particles comprising nanoparticulate drug particles of umeclidinium bromide, vilanterol trifenatate and fluticasone furoate, and nanoparticulate excipient particles of leucine and/or magnesium stearate, wherein the ratio of umeclidinium to vilanterol is 5:1 and further wherein the ratio of umeclidinium to fluticasone furoate is 1.25:1.

Surprisingly, aggregate particles of the present invention may be prepared in the absence of a homogenising surfactant, which may be added to the non-aqueous liquid dispersion prior to, during or after the formation of a dispersion. Absence of a homogenising surfactant simplifies the process by removing the need for a further step to extract this additive. Extraction may also prove difficult and any residual surfactant in the powder compositions for inhaled delivery may pose safety concerns or product stability risks.

In a further aspect of the invention, the aggregate particles are substantially free of a suspension homogenizing surfactant.

As used herein, the term "homogenizing surfactant" means a compound which is dissolved in the non-aqueous liquid dispersing media that reduces the interfacial tension between the liquid and the solid materials dispersed in the liquid media and is used during size reduction processes, e.g. bead milling.

The aggregate particles of the invention may contain one or more binders selected from polymers, dextrans, substituted dextrans, lipids, and/or surfactants. Polymeric binders include, but are not limited to PLGA, PLA, PEG, chitosan, PVP, PVA, hyaluronic acid, DPPC, and DSPC.

As used herein, the term "binder" means a material dissolved in the non-aqueous liquid dispersing media which assists in the maintaining the structural integrity of the individual aggregate particles.

The binder may also play a role in imparting certain characteristics upon the aggregate particles. For example, the aggregates of the present inventions may employ binder materials which are endogenous to the lung, such as DPPC or lecithin, which are approved as generally accepted as safe ("GRAS"). Since they are endogenous to the lung, these materials have the potential to not be perceived as being foreign. Further, by carefully selecting binder materials, it may be possible to alter the dissolution rate of the active therapeutic ingredient(s), potentially affecting the pharmacokinetic and pharmacodynamic (PK/PD) characteristics of the composition.

The binder may also assist in defining a stable and chemically uniform surface. Thus, the aerosol composition may be made with very predictable performance and powder flow characteristics, as the binder may dominate the external physical characteristics and, correspondingly, the physical stability of the composite particles.

Binder, when incorporated into the aggregate particles, makes up from 0.1 to 30% w/w of the composition of the aggregate particles. Preferably, the binder is 20% w/w or less, such as 15, 10, 5, 2.5, or 1% w/w of the composition of the aggregate particles.

The binder may also comprise a quantity of nanoparticulate excipient and/or nanoparticulate drug dissolved in the non-aqueous liquid prior to aggregate particle formation.

Aggregate particles of the present invention may be substantially spherical or irregular, and the particular shape of the aggregate particles may influence product performance. For example, substantially spherical aggregate particles of nanoparticulate drug and, when present, nanoparticulate excipient particles, may have improved dispersion properties over irregular shaped aggregate particles, when blended with a coarse carrier, such as lactose, and delivered from a dry powder inhaler.

In a further aspect of the invention, the aggregate particles are substantially spherical.

In a further aspect of the invention, the aggregate particles are substantially non-spherical or irregular.

Aggregate particles of the present invention are prepared at a suitable size for deposition to the desired area of the respiratory tract. Aggregate particles disclosed herein typically have a mass median aerodynamic diameter of less than 100 μm. Aggregate particles for topical delivery to the bronchiole region of lung typically possess a mass median aerodynamic diameter of less than 10 microns, for example, from about 3 to about 10 microns, such as from about 3 to about 6 microns, for example, from approximately 4 to about 5 microns. Aggregate particles for delivery to the alveolar region typically have a mass median aerodynamic diameter of less than about 3 microns. For example, the compositions for alveolar delivery have a mass median aerodynamic diameter from 1 to 3 microns, for example from about 1 to 2 microns.

As used herein, the term "Mass Median Aerodynamic Diameter" means the median size of a population of particles by mass, where 50% of the particles are above this diameter and 50% are below this diameter, e.g., as determined by laser diffraction, e.g., Malvern, Sympatec.

As used herein, the term "X10" refers to the diameter on a particle size distribution where 10% of the population lies below this size.

As used herein, the term "X50" refers to the median diameter of a particle size distribution where half of the population of particles lies above and half lies below this value.

As used herein, the term "X90" refers to the diameter on a particle size distribution where 90% of the population lies below this size.

In a further aspect of the invention, the aggregate particles have a mass median aerodynamic diameter of about 1 μm to about 6 μm.

The aggregate particles of the present invention may contain 0.01% w/w to 100% w/w of nanoparticulate drug particles, such as 10, 20, 30, 40, 50, 60, 70, 80, 90% w/w of nanoparticulate drug particles.

The aggregate particles of the present invention will typically be administered by inhalation via an inhaler, such as a metered dose inhaler (MDI) or dry powder inhaler (DPI). The aggregate particles may be delivered without further formulation, or they may be admixed with one or more pharmaceutically acceptable excipients to provide a composition for delivery. Suitable excipients include, but are not limited to, amino acids, such as, leucine, iso-leucine, valine, and glycine, sugars, such as lactose, sucrose, glucose and trehalose, poly(aminoacids), such as trileucine, stearates, such as magnesium stearate, calcium stearate and sodium stearate, sugar fatty acid esters, sugar alcohols, such as mannitol, sorbitol, inositol, xylitol, erythritol, lactitol, and malitol, sugar acids, cholesterol, cyclodextrins, EDTA, vitamin E and its derivatives, such as Tocopherols, such as alpha-Tocopherol, gama-Tocopherol, and Tocotrienols, diketo piperazine, taste masking agents, such as aspartame, and inorganic materials. Preferred excipients include, but are not limited, lactose, leucine, magnesium stearate and combinations thereof Excipients, such as lactose, e.g. a-lactose monohydrate, admixed with the aggregate particles to provide a powder composition may form from about 1% w/w to about 99% w/w, for example from about 91% w/w to about 99% w/w of the formulation, such as 92% w/w. In general the particle size of this excipient, for example lactose, will be much greater than the aggregate particles of the present invention. When the carrier is lactose, it will typically be present as milled lactose, having a MMD (mass medium diameter) of 60-90 μm.

The lactose component may comprise a fine lactose fraction. The 'fine' lactose fraction is defined as the fraction of lactose having a particle size less than 7 um, such as less than 6 um, for example less than 5 um. The particle size of the 'fine' lactose fraction may be less than 4.5 um. The fine lactose fraction, if present, may comprise 2 to 10% w/w of the total lactose component, such as 3 to 6% w/w 'fine' lactose, for example 4.5% w/w 'fine' lactose.

Magnesium stearate (MgSt), if present in the composition, is generally used in an amount of about 0.2 to 2% w/w, e.g. 0.6 to 2% w/w or 0.5 to 1.75% w/w, e.g. 0.6%, 0.75%, 1%, 1.25% or 1.5% w/w, based on the total weight of the composition. The magnesium stearate will typically have a particle size in the range 1 to 50 μm, and more particularly 1-20 μm, e.g.1-10 μm. Commercial sources of magnesium stearate include Peter Greven, Covidien/Mallinckodt and FACI.

In a further aspect of the invention, there is provided a powder composition comprising aggregate particles and one or more pharmaceutically acceptable excipients.

In a further aspect of the invention, there is provided a powder composition comprising aggregate particles blended with lactose and/or magnesium stearate.

In one aspect, the present invention provides a powder composition comprising aggregate particles comprising nanoparticulate drug particles of umeclidinium bromide, vilanterol trifenatate and fluticasone furoate.

In a further aspect, the present invention provides a powder composition comprising aggregate particles comprising nanoparticulate drug particles of umeclidinium bromide, vilanterol trifenatate and fluticasone furoate, wherein the ratio of umeclidinium to vilanterol is 5:1 and further wherein the ratio of umeclidinium to fluticasone furoate is 1.25:1.

In yet a further aspect, the present invention provides a powder composition comprising aggregate particles comprising nanoparticulate drug particles of umeclidinium bromide, vilanterol trifenatate and fluticasone furoate, and nanoparticulate excipient particles of one or more excipients.

In yet a further aspect, the present invention provides a powder composition comprising aggregate particles comprising nanoparticulate drug particles of umeclidinium bromide, vilanterol trifenatate and fluticasone furoate, and nanoparticulate excipient particles of leucine and/or magnesium stearate.

In yet a further aspect, the present invention provides a powder composition comprising aggregate particles comprising nanoparticulate drug particles of umeclidinium bromide, vilanterol trifenatate and fluticasone furoate, and nanoparticulate excipient particles of one or more excipients, wherein the ratio of umeclidinium to vilanterol is 5:1 and further wherein the ratio of umeclidinium to fluticasone furoate is 1.25:1.

In yet a further aspect, the present invention provides a powder composition comprising aggregate particles comprising nanoparticulate drug particles of umeclidinium bromide, vilanterol trifenatate and fluticasone furoate, and nanoparticulate excipient particles of leucine and/or magnesium stearate, wherein the ratio of umeclidinium to vilanterol is 5:1 and further wherein the ratio of umeclidinium to fluticasone furoate is 1.25:1.

Aggregate particles, or a powder composition comprising aggregate particles, for administration by dry powder inhaler may be incorporated into a plurality of sealed dose containers provided on medicament pack(s) mounted inside a suitable inhalation device. The containers may be rupturable, peelable or otherwise openable one-at-a-time and the doses of the dry powder composition administered by inhalation on a mouthpiece of the inhalation device, as known in the art.

The medicament pack may take a number of different forms, for instance a disk-shape or an elongate strip. Representative inhalation devices are the DISKHALER™ and DISKUS™ devices, marketed by GlaxoSmithKline. The DISKUS™ inhalation device is, for example, described in GB 2242134A.

Aggregate particles or powder compositions thereof may also be provided as a bulk reservoir in an inhalation device, the device then being provided with a metering mechanism for metering a dose of the composition from the reservoir to an inhalation channel where the metered dose is able to be inhaled by a patient inhaling at a mouthpiece of the device. Exemplary marketed devices of this type are TURBUHALER™ of AstraZeneca, TWISTHALER™ of Schering and CLICKHALER™ of Innovata.

In addition, aggregate particles or powder compositions thereof may be presented in capsules or cartridges (one dose per capsule/cartridge) which are then loaded into an inhalation device, typically by the patient on demand. The device has means to rupture, pierce or otherwise open the capsule so that the dose is able to be entrained into the patient's lung when they inhale at the device mouthpiece. As marketed examples of such devices there may be mentioned ROTAHALER™ of GlaxoSmithKline and HANDIHALER™ of Boehringer Ingelheim.

In addition to delivery from passive devices, aggregate particles or powder compositions thereof may be delivered from active devices, which utilize energy not derived from the patient's inspiratory effort to deliver and deagglomerate the formulation dose.

Aggregate particles of the present invention and powder compositions thereof, may also be delivered as an aerosol from pressurized packs, such as a metered dose inhaler, with the use of a suitable liquefied propellant. Typically, the aerosol composition will comprise the aggregate particles of the present invention, or a powder composition thereof, suspended in a liquefied propellant, such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof The aerosol composition may optionally contain additional formulation excipients well known in the art such as surfactants e.g. oleic acid, lecithin or an oligolactic acid derivative e.g. as described in WO94/21229 and WO98/34596 and/or cosolvents e.g. ethanol. Pressurised formulations will generally be retained in a canister (e.g. an aluminium canister) closed with a valve (e.g. a metering valve) and fitted into an actuator provided with a mouthpiece.

The blending of aggregate particles with carrier to prepare a powder composition and/or the incorporation of aggregate particles or a powder composition thereof into sealed dose containers, such as blisters, is normally performed as part of a fully automated process. Such processing, with the mechanical forces involved, can cause the aggregate particles to fracture leading to a reduction in the fine particle dose. It has surprisingly been found that the inclusion of nanoparticulate magnesium stearate in the aggregate particle constructs improves the robustness of these particles, reducing the risk of fracture during processing.

The reduced risk of fracture associated with the presence of magnesium stearate in the aggregate particle constructs can be observed by scanning electron microscopy (SEM). Samples of aggregate particles or powder compositions before and after processing can be compared. Similarly, samples with differing amounts of magnesium stearate can be compared to show that increasing the amount of magnesium stearate leads to more spherical and more intact aggregate particles after processing. Aggregate particles that are more intact after processing may possess a higher fine particle dose.

Without wishing to be bound by theory, it is hypothesized that aggregate deformation and fracturing leads to a reduction in fine particle dose, as opposed to an increase, because fragments of the aggregates particles adhere more strongly to carrier particles due to their greater surface area and reduced mass. Greater mechanical interlocking may also occur. Such fragments do not separate on subsequent aerosolisation from a dry powder inhaler (DPI). This is supported by deposition data generated using a Next Generation Impactor (NGI), which shows that for poorly performing compositions (i.e. where there is a sign of aggregate particle fracture after processing), drug stage deposition coincides with carrier lactose deposition.

In a further aspect, the present invention provides the use of magnesium stearate in aggregate particles, wherein the aggregate particles comprise nanoparticulates of one or more pharmaceutically active ingredients, to improve the robustness of the aggregate particles.

In a further aspect, the present invention provides the use of magnesium stearate in a dry powder composition, wherein the dry powder composition comprises aggregate particles comprising nanoparticulates of one or more pharmaceutically active ingredients, to improve the robustness of the aggregate particles.

In one aspect, the magnesium stearate is present in nanoparticulate form. Nanoparticulate magnesium stearate (MgSt), if present in the aggregate particles, is generally used in an amount of about 1.0 to 75% w/w, e.g. greater than or equal to 10, 20, 30, 40, 50, 60, or 70% w/w % based on the total weight of the aggregate particles. In one aspect, aggregate particles comprise nanoparticulate magnesium stearate in an amount of about 20.0 to 40.0% w/w.

In another aspect, the present invention provides aggregate particles comprising nanoparticulate drug particles of one or more pharmaceutically active ingredients and nanoparticulate excipient particles, wherein the excipient is magnesium stearate, and further wherein the aggregate particles have an aggregate strength of greater than 0.5 MPa (megapascals).

Suitable pharmaceutically active ingredients include, for example but limited to, beta-agonists, such as salmeterol xinafoate, vilanterol salts (e.g. trifenatate), and formoterol salts (e.g. fumarate); anticholinergics, such as umeclidinium salts (e.g. bromide), tiotropium salts (e.g. bromide) and ipratropium salts (e.g. bromide); and corticosteroids, such as fluticasone propionate, fluticasone furoate, mometasone furoate and ciclesonide. Preferred combinations of pharmaceutically active ingredients include a) umeclidinium bromide and vilanterol trifenatate, b) umeclidinium bromide, vilanterol trifenatate and fluticasone furoate, and c) umeclidinium bromide and fluticasone furoate.

In a further aspect, there is provided a powder composition comprising aggregate particles of the present invention and one or more pharmaceutically acceptable excipients, such as lactose.

In yet a further aspect, there is provided an inhaler comprising aggregate particles or a powder composition of the present invention, wherein the inhaler is a dry powder inhaler or a metered dose inhaler.

The robustness of a particular sample of aggregate particles can be displayed as aggregate strength, measured in MPa units, and can be assessed using a Uniaxial Force Test method. This approach utilizes a Texture Analyzer to compress a sample of the aggregate particles and measure the force required to deform the aggregate particles. In a further aspect, the aggregate strength of a sample of aggregate particles is determined by a Uniaxial Force Test method using a Texture Analyser, comprising the steps:

a) filling the test die (8 mm diameter, 17.0 mm depth) with aggregate particles avoiding compaction of the aggregate particles; and then
b) positioning the upper punch in the start position, just touching the top surface of the aggregate particles; and then
c) initiating the test sequence, wherein the upper punch compresses the aggregate particles at a constant 0.5 mm/second until 240 MPa of stress is achieved, after which the upper punch is withdrawn at 5 mm/second.

In a further aspect of the invention, there is provided a process for the preparation of aggregate particles which comprise nanoparticulate drug particles of umeclidinium bromide, which process comprises:

(a) forming a dispersion of nanoparticulate drug particles and optionally nanoparticulate excipient particles in a non-aqueous liquid, wherein the nanoparticulate drug particles and, when present, the nanoparticulate excipient particles have a solubility of less than 10 mg/ml in said non-aqueous liquid, and wherein the nanoparticulate drug particles and, when present, the nanoparticulate excipient particles have a pre-selected substantially crystalline form, and then
(b) optionally adding one or more binders to the dispersion of step (a); and then
(c) spray-drying the dispersion to generate aggregate particles, wherein the nanoparticulate drug and, when present, nanoparticulate excipient particles have maintained their pre-selected substantially crystalline form.

In a further aspect, aggregate particles of the present invention which comprise nanoparticles of magnesium stearate may be prepared by a process comprising the steps of:

(a) forming a dispersion of nanoparticulate drug particles of one or more pharmaceutically active ingredients and nanoparticulate excipient particles, wherein the excipient is magnesium stearate, in a non-aqueous liquid, and wherein the nanoparticulate drug particles and nanoparticulate excipient particles have a solubility of less than 10 mg/ml in said non-aqueous liquid; and then
(b) spray-drying the dispersion to generate aggregate particles with an aggregate strength of greater than 0.5 MPa.

The non-aqueous liquid in step (a) of the processes, can be any non-aqueous liquid in which each drug and excipient has a solubility of less than 10 mg/ml. Suitable non-aqueous dispersing media include, but are not limited to alcohols, such as ethanol and propanol, ketones, such as acetone and methylethylketone, esters, such as ethyl acetate and isopropylacetate, alkanes (linear or cyclic), such as isooctane, cyclohexane and methylcyclohexane, chlorinated hydrocarbons, such as p11 and p12, fluorinated hydrocarbons, such as p134a and p227, and ethers, such as methyl-tert-butyl ether (MTBE) and cyclopentyl-methyl-ether (CPME). Mixtures of various dispersing media are within the scope of the invention, including mixtures of the classes of media listed above, to achieve the desired environment for the drug and excipient particles. Particularly preferred non-aqueous liquids are those selected from the group consisting of isooctane, cyclohexane, isopropyl acetate, and mixtures thereof.

As used herein, the term "non-aqueous liquid" means a substance which is a liquid other than water (e.g., an organic liquid).

Selection of a non-aqueous liquid in step (a) in which drug and/or excipient particles have a small degree of solubility may provide additional advantages, such as improved crystallinity and sphericity of aggregate particles. In instances where a small amount of drug and/or excipient particles are dissolved in the dispersion, the remaining undissolved crystalline drug and excipient particles in the dispersion may act as seed crystals during the spray drying step, and promote conversion of the dissolved drug and/or excipient material to the desired crystalline form.

In one aspect of the invention, nanoparticulates of drug and, when present, excipient particles are prepared in a bead mill, such as the Cosmo Drais 2. The drug and, when present, excipient particles to be milled are suspended in a non-aqueous liquid. Suitable non-aqueous liquids and the solubility of the drug and excipient material in such media have been described above.

The bead mill is prepared with beads of a given material and bead size in a container of a suitable size. In one aspect of the invention, the beads used in the mill are nylon or yttrium stabilized zirconium oxide beads. Any suitable bead size may be employed in the milling chamber, for example 0.3 mm, or 0 4 mm beads. The suspension is re-circulated through milling chamber using a peristaltic pump. A suitably sized sieve screen may be employed in the bead mill, such as a 0.15 mm size sieve screen, to contain the beads. Mill speed is selected to operate to the appropriate result, for example, at 80% of maximum. The suspension is thus milled and re-circulated until the particle size of the drug has been reduced to the desired size. The operating conditions for the bead mill may be selected in order to achieve the appropriate sized nanoparticles of drug and optionally excipient.

In one aspect of the invention, processes for the preparation of aggregate particles further comprises a step of forming said nanoparticulate drug particles and optionally nanoparticulate excipient particles, wherein said forming step comprises bead milling larger particles of said drug and, when present, said excipient in a non-aqueous liquid to generate nanoparticulate drug particles and, when present, nanoparticulate excipient particles.

In a further aspect of the invention, the particles of drug and excipient are milled separately. If more than one drug is being milled, each drug may be milled separately, or all the drugs may be milled together. Dispersions of milled drug and excipient particles may then be admixed prior to spray-drying.

In yet a further aspect of the invention, the particles of one or more drugs and excipient are milled together, simultaneously. This "co-milling" approach advantageously provides intimate mixing of the nanoparticulate drug and the nanoparticulate excipient.

The effective average particle size of nanoparticulate drug and excipient material in non-aqueous liquid dispersions of the present invention is typically less than 1000 nm, for example less than about 500 nm, 400 nm, 300 nm, 250 nm, 100 nm or 50 nm. In a further aspect of this invention, 50% or more of the nanoparticulate drug particles and/or 50% or more of the nanoparticulate excipient particles in the non-aqueous dispersion have an average particle size of less than 1000 nm prior to spray drying. In a further aspect of the invention, the nanoparticulate drug particles have an effective average particle size of less than about 400 nm. In a further aspect of the invention, the nanoparticulate excipient particles have an effective average particle size of less than about 400 nm.

As used herein, the term "an effective average particle size of less than about 1000 nm" it is meant that at least 50% of the drug particles have a weight average particle size of less than about 1000 nm when measured by light scattering techniques.

The final stage of processing involves preparation of aggregate particles by spray drying a dispersion. Suitable spray driers include the Niro Mobile Minor and PSD-1 spray driers. Co-current and mixed flow drying configurations may be employed. Thus, a Niro Pharmaceutical Spray Drier, Model PSD-1, equipped with an operable peristaltic a Watson Marlow pump 505 may be employed for such purposes. The spray drier may be fitted with a suitable spray nozzle, such as a Spraying Systems two-fluid SU-4 60/100 with 120 cap, or a rotary nozzle.

With the spray nozzle, a two fluid nozzle may employ nitrogen as an atomizing gas. Suitable inlet temperatures for this purpose are also between 80 to 180 degrees Celsius. Other inlet temperatures may be used depending on the physicochemical properties of the non-aqueous feedstock and the feedstock feed rate.

The suspension feedstock may be supplied at a desired feed rate, and the inlet temperatures set as desired. Exemplary feed rates are 30 to 120 mL/min. Rotary nozzles may be operated at up to 35000 RPM.

Nitrogen may also be used as both atomizing gas and the drying gas.

Aggregate particles may be collected using a cyclone or bag filter at the drier outlet and the size of individual particles may be determined by scanning electron microscope (SEM).

The aggregate particles or powder compositions of the present invention may have use in therapy, for example in the treatment of respiratory diseases, such as asthma and COPD.

In a further aspect, the present invention provides aggregate particles for use in the treatment of asthma or COPD.

In a further aspect, the present invention provides powder compositions comprising aggregate particles and one or more pharmaceutically acceptable excipients for use in the treatment of asthma or COPD.

In a further aspect, the present invention provides a method of treating a respiratory disease, such as asthma or COPD, which comprises administering to a human subject in need of treatment a therapeutically effective amount of aggregate particles or a powder composition thereof.

In a further aspect, the present invention provides the use of aggregate particles for the manufacture of a medicament for treatment of a respiratory disease, such as asthma or COPD.

As used herein, the term "treatment" refers to prophylaxis of a disease, ameliorating or stabilising a disease, reducing or eliminating the symptoms of a disease, slowing or eliminating the progression of a disease, and preventing or delaying reoccurrence of a disease in a previously afflicted human subject.

EXAMPLES

The following examples are given to illustrate the present invention. It should be understood, however, that the invention is not to be limited to the specific conditions or details described in these examples.

Compound A (also API-A) is umeclidinium bromide, also referred to as 4-[hydroxy(diphenyl)methyl]-1-{2-[(phenylmethyl)oxy]ethyl}-1-azoniabicyclo[2.2.2]octane bromide, which may be prepared according to Example 84 in International Patent Publication No. WO 2005/104745 (US 2007/0185155 A1), incorporated herein by reference.

Compound B (also API-B) is fluticasone furoate, also referred to as 6α,9α-difluoro-17α-[(2-furanylcarbonyl)oxy]-11β-hydroxy-16α-methyl-3-oxo-androsta-1,4-diene-17β-carbothioic acid S-fluoromethyl ester, which may be prepared according to Example 1 in International Patent Publication No. WO02/12265 (US 2003/045512 A1), incorporated herein by reference.

Compound C (also API-C) is vilanterol trifenatate, also referred to as 4-{(1R)-2-[(6-{2-[(2,6-dichlorobenzyl)oxy]ethoxy}-hexyl)amino]-1 -hydroxyethyl}-2-(hydroxymethyl)phenol triphenylacetate, which may be prepared according to Example 78(i) in International Patent Publication No. WO 03/024439 (US 2005/075394A), incorporated herein by reference.

Sample Preparation

The aggregate particles listed in Table 1, with the exception of Sample 5, were manufactured using a non-aqueous bead milling process followed by spray drying.

A Netzsch MiniCer Mill or a Drais Cosmo 2 Mill was used. The mill was setup using the parameters listed in Table 2. Drugs and excipients were weighed into a suitable container. Non-aqueous liquid media was added to the container and the contents shaken until all powder was visibly wetted. The suspension was poured into the mill reservoir where liquid vehicle was already re-circulating. The suspension was milled for the desired duration, and then collected. In all examples, drug and excipient materials were co-milled together in the mill. Suspensions were stored in a closed container at ambient conditions until spray drying was performed. Table 4 lists the suspensions prepared.

Spray drying was performed using either a Buchi B-290 dryer or a Niro PSD-1 dryer. Table 3 lists the dryer parameters used. Spray drying is advantageously suitable for fabricating such aggregate particles. The size of the aggregates can be controlled by the spray drying conditions, independent of the drug and excipient. The flexibility and control associated with spray drying, may allow production of particles with desirable aerodynamic properties, thus permitting high efficiency delivery of medicaments. Powder was collected in a container beneath the cyclone.

Conversion factors between the salt and base for compounds A, B and C were 1.194, 1 and 1.592, respectively.

TABLE 1

Aggregate Particle Preparation

| Sample | Compound A % w/w[a] | Compound B % w/w[a] | Compound C % w/w[a] | Excipient 1 | Excipient 1 % w/w | Excipient 2 | Excipient 2 % w/w |
|---|---|---|---|---|---|---|---|
| 1 | 4.2 | 3.3 | — | Leucine | 92.5 | — | — |
| 2 | 50 | 40 | 10 | — | — | — | — |
| 3 | 50 | 40 | 10 | — | — | — | — |
| 4 | 50 | 40 | 10 | — | — | — | — |
| 5 | 50 | 40 | 10 | — | — | — | — |
| 6 | 3.75 | 3 | 0.75 | Leucine | 92.5 | | |
| 7 | 45 | 36 | 9 | MgSt | 10 | — | — |
| 8 | 3.75 | 3 | 0.75 | MgSt | 7.5 | Leucine | 85 |
| 9 | 3.75 | 3 | 0.75 | MgSt | 7.5 | Lactose | 85 |
| 10 | 25 | 20 | 5 | MgSt | 10 | Leucine | 40 |

[a]Concentrations listed are for each drug in the base form.

TABLE 2

| Mill Parameters | |
|---|---|
| Grinding Media | 0.3 mm or 0.4 mm yttrium stabilized zirconium oxide grinding beads |
| Configuration | Suspension re-circulated between reservoir and milling chamber using a peristaltic pump |

TABLE 2-continued

| Mill Parameters | | |
|---|---|---|
| | A stirrer was used to mix contents of reservoir during processing | |
| Sieve Screen Size | 0.15 mm | |
| Mill Speed | MiniCer = 1500-2500 RPMs | Cosmo 2 = 80% |
| Recirculating Pump Speed Setting | MiniCer = 3 | Cosmo 2 = 9 |

TABLE 3

Spray Dryers and Operating Parameters

| | | |
|---|---|---|
| Dryer | Buchi B-290 Dryer with integral pump | Niro Pharmaceutical Spray Dryer (Model PSD-1) |
| Feed pump | | Watson Marlow pump 505L |
| Collection method | High efficiency cyclone | High efficiency cyclone |
| Drying Nitrogen Flow Rate | Approximately 600 L/min | 75 kg/hr |
| Inlet Temperature (Celsius) | 150-210 | 180 |
| Outlet Temperature (Celsius) | 80-90 | 95 |
| Atomizer | Buchi 0.7 mm nozzle; 1.5 mm cap | Two fluid nozzle: Spraying Systems Co., Top spray 60/100 with 120 cap |
| Atomization Pressure (psi) | Approximately 58 | 50.75 |
| Suspension feed rate (mL/min) | 10-12 | 60 |

TABLE 4

Suspension Feedstocks for Spray-Drying

| | | | Quantity | | | | | | | Approx. |
|---|---|---|---|---|---|---|---|---|---|---|
| Sample | Suspension Feedstock[a] | Vehicle | Compound A (g) | Compound B (g) | Compound C (g) | Excipient 1 (g) | Excipient 2 (g) | Vehicle (mL) | Bead Mill/ Dryer | Milling Time (hours) |
| 1[b] | 0.25% w/v API-A + 0.17% w/v API-B + 4.6% w/v leucine | Isooctane | 1.0 | 0.7 | — | 18.4 (leucine) | — | 400 | MiniCer/ Buchi | 0.7 |
| 2 | 2.6% w/v API-A + 1.7% w/v API-B + 0.7% w/v API-C | Cyclohexane | 10.3 | 6.9 | 2.8 | — | — | 400 | MiniCer/ Buchi | 0.7 |
| 3 | 2.6% w/v API-A + 1.7% w/v API-B + 0.7% w/v API-C | 25/75 Isopropyl-acetate/ cyclohexane | 10.3 | 6.9 | 2.8 | — | — | 400 | MiniCer / Buchi | 1 |
| 4 | 2.6% w/v API-A + 1.7% w/v API-B + 0.7% w/v API-C | 50/50 Isopropyl-acetate/ cyclohexane | 10.3 | 6.9 | 2.8 | — | — | 400 | MiniCer/ Buchi | 1 |
| 5 | 2.6% w/v API-A + 1 .7% w/v API-B + 0.7% w/v API-C | 18/82 2-propanol/water | 31.0 | 20.8 | 8.3 | — | — | 1200 | Cosmo2/ PSD-1 | 3 |
| 6[b] | 0.22% w/v API-A + 0.15% w/v API-B + 0.06% w/v API-C + 4.6% w/v leucine | Isooctane | 0.9 | 0.6 | 0.2 | 18.3 (leucine) | — | 400 | MiniCer/ Buchi | 0.7 |
| 7 | 2.4% w/v API-A + 1.6% w/v API-B + 0.6% w/v API-C + 0.4% w/v MgSt | Isooctane | 28.2 | 19.0 | 7.6 | 5.3 (MgSt) | — | 1200 | Cosmo2/ PSD-1 | 2 |
| 8[b] | 0.22% w/v API-A + 0.15% w/v API-B + 0.06% w/v API-C + 0.37% w/v MgSt + 4.2% w/v leucine | Isooctane | 0.9 | 0.6 | 0.2 | 1.5 (MgSt) | 16.8 (leucine) | 400 | MiniCer/ Buchi | 0.7 |
| 9[b] | 0.22% w/v API-A + 0.15% w/vAPI-B + 0.06% w/v API-C + | Isooctane | 0.9 | 0.6 | 0.2 | 1.5 (MgSt) | 16.8 (lactose) | 400 | MiniCer/ Buchi | 0.7 |

TABLE 4-continued

Suspension Feedstocks for Spray-Drying

| Sample | Suspension Feedstock[a] | Vehicle | Quantity Compound A (g) | Compound B (g) | Compound C (g) | Excipient 1 (g) | Excipient 2 (g) | Vehicle (mL) | Bead Mill/ Dryer | Approx. Milling Time (hours) |
|---|---|---|---|---|---|---|---|---|---|---|
| 10 | 0.37% w/v MgSt + 4.2% w/v lactose 1.38% w/v API-A + 0.93% w/v API-B + 0.37% w/v API-C + 0.46% w/v MgSt + 1.86% w/v leucine | 25/75 Isopropyl-acetate/ cyclohexane | 6.9 | 4.6 | 1.8 | 2.3 (MgSt) | 9.3 (leucine) | 500 | MiniCer/ Buchi | 1.25 |

[a]Concentrations listed are for API in the salt form.
[b]Excipient slurry was milled for 25 minutes prior to API slurry addition.

Sample Analysis

The crystallinity and the form of the powder samples described in Table 1 were measured by X-Ray Powder Diffraction (XRPD).

The particle size distribution (PSD) of the powder samples was measured by a dry laser diffraction method using a Sympatec Particle Size Instrument.

Aggregate particle robustness was measured using an Uniaxial Force Test method developed utilizing the Texture Analyzer instrument from Stable Micro Systems. This method measures the collapse of the macro structure of porous particles and not the intrinsic mechanical properties. Table 5 lists the method components and settings. The Texture Analyser is a highly sensitive force/displacement instrument able to accept a range of single sided load cells. The equipment is designed such that different probes can be attached to the force transducer to measure tension or compression of the test sample as a function of probe distance, speed and profile. The equipment for the compression test comprised Manesty F tablet tooling (punches and die) combined with accessories available from the manufacturers of the Texture Analyser (Stable Micro Systems). Compensation for errors associated with deformation of the load cell and other components was undertaken automatically with deflection correction, or frame stiffness calibration. The punch faces and die bore were lubricated prior to each analysis with a suspension of Magnesium Stearate in Acetone. The solvent was allowed to evaporate before testing.

TABLE 5

Uniaxial Force Test Components and Settings

| | |
|---|---|
| Instrument | Texture Analyser TA.HD Plus or similar: Uniaxial, single sided, force/distance analysis. Driven upper punch with top located load cell |
| Load Cell | 250 kg located on the upper punch |
| Lower Punch | 8 mm diameter, round, plain, flat face |
| Upper Punch | 8 mm diameter, round, plain, flat face |
| Test Die | 8 mm diameter by 17.0 mm deep, depth achieved through the use of spacers under the lower punch |
| Test speed | 0.5 mm/second |
| Post test speed | 5 mm/second |
| Measurement mode | Force in compression |
| Punch/die friction limits | Less than or equal to 200 grams reactive force with un-lubricated tooling |

Prior to batch testing, the upper punch position was calibrated by taring its position in relation to the lower punch face, i.e. punch face to face contact was zero distance. Subsequently, the die surface position was measured relative to the zero point. This provided an exact fill depth measurement of the die. The method procedure is outlined below:

a. Test sample was filled into the die until exactly level with the die surface without densifying or compacting the sample. This was achieved by pouring tumbled powder into the die until it was slightly proud of the die surface and the surplus was then cut off using a flat blade.

b. The upper punch was moved to the test start position, level with the previously calibrated die surface position. The upper punch was therefore just touching the surface of the loose filled test sample.

c. The test sequence was initiated. The upper punch compressed the sample at a constant 0.5 mm/second until 240 MPa of stress was reached. The punch was then withdrawn at 5 mm/second. The stress (MPa) against distance (mm) was recorded during the test at a typical 50 points per second.

d. Following the test the compressed sample was ejected as a rigid compact and weighed.

Aggregate particle strength is determined by applying the equations:

$$C=\left(\frac{Vo\cdot V}{Vo}\right)=\frac{abP}{1+bP}\longrightarrow C+bPC=abP\longrightarrow\frac{1}{ab}+\frac{P}{a}=\frac{P}{C}$$

Where Vo is the compacted volume of the bed (the volume at an applied pressure at 0.02 MPa), V is the continuous volume at an applied stress P, a and b are constants. Constant 1/b (with units of pressure) relates to the yield stress of individual powder particles.

By plotting P/C with P the constants a and b can be derived, 1/a being the slope and 1/ab the intercept. 1/b×0.7 has been found to correlated with mean aggregate strength in units of pressure (MPa). The application of these calculations are illustrated in Tables 6 through 9.

TABLE 6

| Calculation of C | | | | | | | |
|---|---|---|---|---|---|---|---|
| Value | $V_0$ | $V_1$ | $V_2$ | $V_5$ | $C_1$ | $C_2$ | $C_5$ |
| Description | The volume of the die at 0.02 MPa ($cm^3$) | The volume of the die at 1 MPa ($cm^3$) | The volume of the die at 2 MPa ($cm^3$) | The volume of the die at 5 MPa ($cm^3$) | $\frac{V_0 - V_1}{V_0} = C_1$ | $\frac{V_0 - V_2}{V_0} = C_2$ | $\frac{V_0 - V_5}{V_0} = C_5$ |
| Calculation Detail | $V_0$ = (1.7 − Travel at Pressure $P_n$) x 0.50265 Subtracting the travel at each pressure (0.02 MPa, 1 MPa, 2 MPa and 5 MPa) from the total empty cell height gives the powder depth e.g. 1.7 cm − travel from die surface to 0.02 MPa in cm Multiplying the powder depth by the cross sectional area of the die gives $V_n$. The area is 0.50265 $cm^2$ for an 8 mm die. | | | | The value C is simply the relative volume change in the powder at a given stress or pressure P. | | |

TABLE 7

| Calculation of P/C | | | |
|---|---|---|---|
| Value | $P/C_{(1)}$ | $P/C_{(2)}$ | $P/C_{(5)}$ |
| Calculation Detail | $P_{1\ MPa}/C_1$ The Pressure (P) divided by the Kawakita value (C) at each stress | $P_{2\ MPa}/C_1$ | $P_{5\ MPa}/C_1$ |

TABLE 8

| Calculation of 1/a, 1/ab, a and b | | | | |
|---|---|---|---|---|
| Value | 1/a | 1/ab | a | b |
| Description | The slope of P/C plotted against P between 1 MPa and 5 MPa | The y intercept of P/C plotted against P | The reciprocal of 1/a | Derivation of b from a and 1/ab |
| Calculation | $\frac{P/C_{(5)} - P/C_{(1)}}{P_{(5)} - P_{(1)}} = /a$ | $P/C_{(5)} - (/a \cdot P_{(5)}) = /ab$ | $\frac{1}{1/a} = a$ | $\frac{1}{a \cdot 1/ab} = b$ |
| Detail | The slope in the range of P/C from 1 MPa and 5 MPa plotted against the corresponding pressures | Any point on the stress range could be used for the calculation. For consistency values of P/C and P at 5 MPa have been used, therefore where P = 5 MPa use the value of P/C at 5 MPa. | | |

TABLE 9

| Calculation of 1/b and aggregate particle strength | | |
|---|---|---|
| Value | 1/b | Aggregate strength |
| Description | The reciprocal of b | Offset correction to calculate collapse strength in units of pressure from 1/b |
| Calculation | $\frac{1}{b} = /b$ | 0.7 × /b = Strength (MPa) |

Note:
MPa = megapascals

The aerodynamic performance of select powders described in Table 1 was determined by cascade impaction. Powders comprised of aggregated particles were blended with carrier lactose using a Turbula Type T2F blender. Blends were filled into blister strips and assembled in Diskus devices. Doses were delivered into a Next Generation Impactor operating at 60 L/min or a Fast Screening Impactor operating at 60 L/min (both commercially available from MSP Corp (Shoreview, Minn., USA)). Aerodynamic performance results are listed in Table 11 as percent fine particle dose (%FPD) of the nominal dose.

Materials

L-Leucine was obtained from Sigma Aldrich and was coarsely ground using a mortar and pestle prior to use in suspension manufacturing. Lactose monohydrate was obtained from Freisland Foods Domo Ltd. Isooctane, cyclohexane and isopropyl acetate was obtained from Sigma Aldrich. The magnesium stearate grade was LIGA, MF-2-V premium.

FIGS. 1 and 2 display the XRPD patterns for the input APIs and the input excipients, respectively.

Example 1

The purpose of this example was to demonstrate the technique of manufacturing three-component aggregate particles comprised of two different drug substances and an excipient. Sample 1 was comprised of Compound A, Compound B and leucine (Tables 1 and 4).

FIG. 3 displays a typical SEM micrograph of Sample 1 spray dried particles. Particles were generally irregular in shape.

FIG. 4 shows the XRPD pattern for Sample 1 after spray drying. This manufacturing approach maintains the preselected crystallinity of the input powders and produces substantially crystalline product. Table 10 lists the PSD results. The results suggested that these particles were within the respirable size range.

Example 2

The purpose of this example was to demonstrate the technique of manufacturing three-component respiratory particles comprised of three different nanoparticulate drugs. Samples 2 through 5 were produced by bead milling APIs in different vehicles, then spray drying. An API content of 50% w/w Compound A, 40% w/w, Compound B and 10% w/w Compound C was targeted in the spray dried powder.

FIG. 5 displays typical SEM micrographs of Samples 2, 3 and 4. The spray dried particles were spherical to irregular in shape. Samples 2, 3 and 4 demonstrate how the shape of the aggregate particles may be influenced by the solubility of the APIs in the vehicle. Room temperature (22° C.) solubility measurements of the APIs in cyclohexane and in 25:75 and 50:50 mixtures of isopropyl acetate (IPAc):cyclohexane showed that the total percent of API in solution increased from 0.1% to approximately 0.8% when moving from a cyclohexane system to a 50:50 IPAc:cyclohexane system. During spray drying, the low level of solubilised API precipitated out and acted as a binder to improve the structural integrity of the aggregate particles. Improved structural integrity was exhibited by an increase in aggregate particle sphericity (see Sample 4 in FIG. 5). Improved particle robustness/sphericity may improve the control in the manufacturing process and produce more consistent product performance.

FIG. 6 shows the XRPD patterns for Samples 2, 3 and 4 after spray drying. This manufacturing approach maintains the preselected crystallinity of the input powders and produces substantially crystalline product. The XRPD patterns also demonstrate how the crystallinity of the powder may be adjusted by selecting the appropriate vehicle.

Table 10 lists the PSD results for Samples 3 and 4. Following spray drying, the three-component particles were within the respirable size range. Because Sample 5 was prepared using an aqueous vehicle having greater surface tension, the size distribution of this sample was relatively larger than the samples prepared using organic vehicles.

The aerodynamic performance of select aggregate particles was determined Samples 3 and 4 were used to prepare approximately 2% w/w blends of aggregated particles in lactose carrier. Blends were prepared using a Turbula blender. Table 11 describes the content of the blends, determined by HPLC analysis. A conventional blend (Sample 11) was prepared using micronized APIs and a high shear blender at a similar strength for comparison purposes. Blends were filled into blister strips and delivered from a Diskus Device into a Next Generation Impactor operating at 60 litres per minute. Table 11 lists the fine particle dose (%FPD) measured.

The APIs in the conventional blend exhibited greater variation in % fine particle dose due to the drugs existing as discrete particles within the blend. In contrast the APIs in Samples 3, and 4 displayed near identical fine particle doses, as a result of the APIs being bound in the aggregate particles. From a product development standpoint, this approach enhances the predictability of performance, allowing the drugs in the aggregate particles to have the same % fine particle dose each time. This may provide therapeutic advantages, such as enhanced efficacy/synergy, since this would allow for co-deposition to the same regions of the airways. In contrast, the performance of discretely blended micronized API is dependent on both the particle size distribution of each drug but also the interaction of each drug with all the components of the blend, which makes targeting identical performance highly challenging.

Example 3

The purpose of this example was to demonstrate the technique of manufacturing four-component respiratory particles comprised of three nanoparticulate drugs, and a nanoparticulate excipient.

Samples 6 and 7 used a co-milling approach in which the drugs and excipient was bead milled together in isooctane. Sample 6 incorporated 92.5% w/w leucine in the spray dried aggregate particle, while Sample 7 incorporated 10% w/w MgSt. In both cases, the ratio of Compound A:Compound B:Compound C was maintained at 5:4:1 within the aggregate particle and the excipient content varied.

FIG. 7 displays typical SEM micrographs of the spray dried particles. The spray dried particles were spherical to irregular in shape. The PSD results (Table 10) suggested the spray dried particles were within the respirable size range. These results demonstrate how excipient may be easily incorporated into the aggregate particle across a range of concentrations while controlling the API content and ratios amongst APIs.

XRPD patterns for samples 6 and 7 are provided in FIG. 8. The crystallinity of Sample 7 could be further enhanced by optimizing the non-aqueous vehicle.

Example 4

The purpose of this example was to demonstrate the technique of manufacturing five-component respiratory particles comprised of three nanoparticulate drugs, and two nanoparticulate excipients. Samples 8, 9 and 10 used a co-milling approach in which the drugs and excipients were bead milled together. Samples 8 and 9 were milled in isooctane while Sample 10 was prepared using a mixture of 25:75 isopropyl actetate:cyclohexane as the vehicle.

FIG. 9 displays typical SEM micrographs of the spray dried particles. The spray dried particles were spherical to irregular in shape. The PSD results (Table 10) suggested the spray dried particles were within the respirable size range. These results demonstrate how multiple excipients may be easily incorporated into the aggregate particle.

XRPD patterns for samples 8, 9 and 10 are provided in FIG. 10.

Example 5

The purpose of this example is to illustrate the chemical stability benefit provided by this manufacturing approach. The chemical stability of Sample 5 and Sample 7 as neat aggregate particles and as lactose blends (described in Table 11) were evaluated by placing aliquots of bulk powder on stability storage. Blends were prepared using a Turbula blender at approximate 2% w/w aggregate particles in lactose concentration. Aliquots were either stored unprotected at 25° C./60% RH or overwrapped with silica desiccant at 30° C./65% RH and 40° C./75% RH. Total impurities were measured at initial for the aggregate and at select time points for up to 3 months. For comparison, a conventional blend was prepared using micronized APIs and the Turbula blender. The blend contained 2% w/w API-A, 1.7% w/w API-B, and 0.4% w/w API-C in lactose and was tested in parallel. FIG. 11 displays the chemical stability results. Aerodynamic performance testing was not performed on this conventional blend. The micronized API blend showed an increase in total impurities despite overwrap protection. Impurities increased from approximately 0.5% area/area to approximately 4.4% area/area after 3 months at 30° C./65% RH. This was primarily due to a chemical interaction between API-C and lactose. The groups containing Sample 5 and Sample 7 showed no significant increase in impurities over the same three month storage period. Formulating API-C into aggregate particles provided improved chemical stability compared to the conventional micronized API approach.

Example 6

The purpose of this example was to illustrate the stability benefit offered by this manufacturing approach. The physical and chemical stability of Sample 10 was evaluated. Sample 10 was used to prepare a 4% w/w blend of aggregated particles in lactose carrier (2% w/w total API). The blend was prepared using a Turbula blender. Table 11 describes the content of the blend, determined by HPLC analysis. Blends were filled into blister strips using semi-automated filling equipment and placed on stability. Blister strips were placed either unprotected or overwrapped with silica desiccant in a 30° C./65% RH chamber for up to six months. Formulations were evaluated for physical stability at select time points by delivering doses using a Diskus Device into a Fast Screening Impactor operating at 60 litres per minute. FIG. 12 displays the physical stability results. No significant change in formulation performance was observed in either protected or unprotected strips.

Blister strips were tested for chemical stability by testing total impurities at select time points. FIG. 13 displays the chemical stability results. No significant increase in total impurities was observed in either protected or exposed strips. As in Example 5, the increase in impurities that typically accompanies formulating micronized API-C with lactose carrier was not seen using this aggregate nanoparticles approach.

TABLE 10

Particle Size Distribution of Powder Compositions

| Sample | Composition (% w/w) | Spray Drier | Mean PSD Results X10 (microns) | X50 (microns) | X90 (microns) |
|---|---|---|---|---|---|
| 1 | (4.2:3.3:92.5) API-A:API-B:leucine | Buchi | 0.7 | 1.5 | 3.3 |
| 2 | (50:40:10) API-A:API-B:API-C | Buchi | NT | NT | NT |
| 3 | (50:40:10) API-A:API-B:API-C | Buchi | 0.7 | 1.9 | 4.4 |
| 4 | (50:40:10) API-A:API-B:API-C | Buchi | 0.8 | 1.8 | 4.1 |
| 5 | (50:40:10) API-A:API-B:API-C | PSD-1 | 0.8 | 2.5 | 8.5 |
| 6 | (3.75:3:0.75:92.5) API-A:API-B:API-C:leucine | Buchi | 0.8 | 1.7 | 3.4 |
| 7 | (45:36:9:10) API-A:API-B:API-C:MgSt | PSD-1 | 0.6 | 1.3 | 2.5 |
| 8 | (3.75:3:0.75:7.5:85) API-A:API-B:API-C:MgSt:leucine | Buchi | 0.9 | 1.8 | 3.4 |
| 9 | (3.75:3:0.75:7.5:85) API-A:API-B:API-C:MgSt:lactose | Buchi | 0.8 | 1.6 | 3.0 |
| 10 | (25:20:5:10:40) API-A:API-B:API-C:MgSt:leucine | Buchi | 0.9 | 2.1 | 4.8 |

NT = not tested.

TABLE 11

Physical Properties and Aerodynamic Performance of Powder Compositions

| Sample | Composition (% w/w) | API content in blend (% w/w) API-A | API-B | API-C | % FPD of Nominal[b] (%) API-A | API-B | API-C |
|---|---|---|---|---|---|---|---|
| 3 | (50:40:10) API-A:API-B:API-C | 0.94 | 0.76 | 0.19 | 22.3 | 22.3 | 21.0 |
| 4 | (50:40:10) API-A:API-B:API-C | 0.94 | 0.74 | 0.19 | 32.3 | 32.3 | 32.0 |
| 5 | (50:40:10) API-A:API-B:API-C | 0.85[c] | 0.69[c] | 0.17[c] | 37.7 | 39 | 36 |
| 7 | (45:36:9:10) API-A:API-B:API-C:MgSt[d] | 0.85 | 0.72 | 0.17 | 40.0 | 40.0 | 37.0 |
| 10 | (25:20:5:10:40) API-A:API-B:API-C:MgSt:leucine | 1.02 | 0.83 | 0.20 | 45.2 | 45.2 | 44.6 |
| 11[a] | 1% w/w API-A + 0.8% w/w API-B + 0.2% w/w API-C in Lactose Carrier | 1.04 | 0.84 | 0.21 | 31.8 | 24.9 | 28.8 |

[a]Micronized APIs used..
[b]Diskus device delivered into NGI or FSI at 60 LPM.
[c]Content calculated based on API content in aggregate and 2% target blend strength.
[d]MgSt concentration in blend was approximately 0.2% w/w.
% FPD = Percent fine particle dose <5 microns.

Example 7

The purpose of this example was to illustrate the effect of MgSt on the robustness and performance of aggregate particles. Three component aggregates consisting of Compound A, and varying concentrations of MgSt and leucine were prepared (see Tables 12 and 13). FIG. 14 displays typical SEM micrographs of the spray dried particles. The spray dried particles were spherical to irregular in shape. The PSD results in Table 14 suggested the spray dried particles were within the respirable size range. XRPD patterns are provided in FIG. 15 and were found to be substantially crystalline.

Samples 12, 13 and 14 were assessed for aggregate strength using the Uniaxial Force Test method previously described. This data provides an indication of the robustness of the aggregate particles. As seen in Table 15, aggregate particle strength was found, surprisingly, to increase with increasing MgSt concentration and decreasing leucine concentration.

Aerodynamic performance was evaluated by blending aggregate particles with lactose carrier at a 2% w/w aggregate (1% w/w API-A concentration) and filling blends into blister strips using semi-automated filling equipment. Doses were delivered from a Diskus device into a Fast Screening Impactor operating at 60 liters-per-minute. The fine particle dose was observed to increase with increasing MgSt concentration and increasing aggregate particle strength (Table 15). Without wishing to be bound by theory, it is hypothesised that the observed improvement in respirable dose is due in part to the increased robustness of the aggregate particles, which are less prone to fracture during blending and filling steps. The inclusion of magnesium stearate may, in addition, reduce the adhesion of aggregate particles to the carrier (e.g. lactose) surfaces. FIG. 16 shows SEMs of the blend powders after filling into blister strips. A greater number of spherical constructs are observed in the SEMs in line with the increasing MgSt concentration and aggregate strength.

TABLE 12

Aggregate Particles Prepared With Varying MgSt Concentration

| Sample | Compound A % w/w[a] | Excipient 1 | Excipient 1 % w/w | Excipient 2 | Excipient 2 % w/w |
|---|---|---|---|---|---|
| 12 | 50 | MgSt | 10 | Leucine | 40 |
| 13 | 50 | MgSt | 20 | Leucine | 30 |
| 14 | 50 | MgSt | 30 | Leucine | 20 |

[a]Concentrations listed are for Compound A are in the salt form.

TABLE 13

Suspension Feedstocks for Samples 11, 12 and 13

| Sample | Suspension Feedstock[a] | Vehicle | Quantity: Compound A (g) | Quantity: Excipient 1 (g) | Quantity: Excipient 2 (g) | Quantity: Vehicle (mL) | Bead Mill/ Dryer | Approx. Milling Time (hours) |
|---|---|---|---|---|---|---|---|---|
| 12 | 2.5% w/v API-A + 0.5% w/v MgSt + 2.0% w/v leucine | Isooctane | 12.5 | 2.5 (MgSt) | 10 (Leucine) | 500 | MiniCer/ Buchi | 1.5 |
| 13 | 2.5% w/v API-A + 1.0% w/v MgSt + 1.5% w/v leucine | Isooctane | 12.5 | 5.0 (MgSt) | 7.5 (Leucine) | 500 | MiniCer/ Buchi | 1.5 |
| 14 | 2.5% w/v API-A + 1.5% w/v MgSt + 1.0 w/v leucine | Isooctane | 12.5 | 7.5 (MgSt) | 5.0 (Leucine) | 500 | MiniCer/ Buchi | 1.5 |

[a]Concentrations listed are for the salt form of API-A.

TABLE 14

Particle Size Distribution of Samples 11, 12 and 13

| Sample | Composition (% w/w) | Spray Drier | Mean PSD Results: X10 (microns) | Mean PSD Results: X50 (microns) | Mean PSD Results: X90 (microns) |
|---|---|---|---|---|---|
| 12 | (50:10:40) API-A:MgSt:leucine | Buchi | 1.0 | 2.1 | 3.8 |
| 13 | (50:20:30) API-A:MgSt:leucine | Buchi | 1.0 | 2.1 | 4.2 |
| 14 | (50:30:20) API-A:MgSt:leucine | Buchi | 0.9 | 1.9 | 4.0 |

TABLE 15

Physical Properties and Aerodynamic Performance of Samples 11, 12 and 13

| Sample | Composition (% w/w) | Aggregate Strength (MPa) | API-A content in blend (% w/w) | % FPD of Nominal (%) |
|---|---|---|---|---|
| 12 | (50:10:40) API-A:MgSt:leucine | 0.41 | 1.68 | 19 |
| 13 | (50:20:30) API-A:MgSt:leucine | 0.59 | 1.55 | 51 |
| 14 | (50:30:20) API-A:MgSt:leucine | 0.61 | 1.73 | 71 |

% FPD = Percent fine particle dose < 5 microns.

The invention claimed is:

1. Aggregate particles comprising nanoparticulate drug particles of umeclidinium bromide, vilanterol trifenatate and fluticasone furoate, wherein the aggregate particles have a mass median aerodynamic diameter of less than about 100 μm and are substantially free of a suspension homogenizing surfactant, and further wherein the nanoparticulate drug particles have an effective average particle size of less than about 1000 nm.

2. The aggregate particles of claim 1, wherein the ratio of umeclidinium to vilanterol is 5:1.

3. The aggregate particles of claim 1, wherein the ratio of umeclidinium to fluticasone furoate is 1.25:1.

4. The aggregate particles of claim 2, wherein the ratio of umeclidinium to fluticasone furoate is 1.25:1.

5. The aggregate particles of claim 1, wherein the aggregate particles further comprise nanoparticulate excipient particles of one or more excipients.

6. The aggregate particles of claim 5, wherein the nanoparticulate excipient particles comprise magnesium stearate.

7. The aggregate particles of claim 1, wherein the aggregate particles have a mass median aerodynamic diameter of about 1 μm to about 6 μm.

8. The aggregate particles of claim 1, wherein the nanoparticulate drug particles have an effective average particle size of less than about 400 nm.

9. A powder composition comprising aggregate particles of claim 1, and one or more pharmaceutically acceptable excipients.

10. The powder composition of claim 9, wherein the pharmaceutically acceptable excipient comprises lactose and, optionally, magnesium stearate.

11. An inhaler comprising aggregate particles according to any one of claims 1 to 8, wherein the inhaler is a dry powder inhaler or metered dose inhaler.

12. A process for the preparation of aggregate particles, according to any of claims 1 to 8, which process comprises:

(a) forming a dispersion of nanoparticulate drug particles and optionally nanoparticulate excipient particles in a non-aqueous liquid substantially free of a suspension homogenizing surfactant, wherein the nanoparticulate drug particles and, when present, the nanoparticulate excipient particles have a solubility of less than 10 mg/ml in said non-aqueous liquid, and wherein the nanoparticulate drug particles and, when present, the nanoparticulate excipient particles have a pre-selected substantially crystalline form, and then (b) optionally adding one or more binders to the dispersion of step (a); and then (c) spray-drying the dispersion to generate aggregate particles, wherein the nanoparticulate drug and, when present, nanoparticulate excipient particles have maintained their pre-selected substantially crystalline form, and said aggregate particles are substantially free of a suspension homogenizing surfactant.

13. The process of claim 12, further comprising a step of forming said nanoparticulate drug particles and optionally nanoparticulate excipient particles, wherein said forming step comprises bead milling larger particles of said drug and, when present, said excipient in a non-aqueous liquid to generate nanoparticulate drug particles and, when present, nanoparticulate excipient particles.

14. The process of claim 12, wherein the nanoparticulate drug particles have an effective average particle size of less than about 400 nm.

15. The process of claim 12, wherein the non-aqueous liquid is selected from the group consisting of isooctane, cyclohexane, isopropyl acetate, and mixtures thereof.

16. A method of treating an inflammatory disease or condition in the lung of a human in need thereof comprising the administration of aggregate particles as defined in any of claims 1 to 8 via inhalation.

17. A method of improving the robustness of aggregate particles, which have a mass median aerodynamic diameter of less than about 100 μm, wherein the aggregate particles comprise nanoparticulate drug particles of one or more pharmaceutically active ingredients which have an effective average particle size of less than about 1000 nm, wherein said method comprises inclusion of magnesium stearate in the aggregate particle.

18. The method according to claim 17 wherein the one or more pharmaceutically active ingredients are selected from the group consisting of beta-agonists, anticholinergics and corticosteroids.

19. The method according to claim 17, wherein the aggregate particles comprise magnesium stearate in an amount of about 20.0 to 40.0% w/w.

20. The method according to claim 17, wherein the aggregate particles have a mass median aerodynamic diameter of about 1 μm to about 6 μm.

21. The method according to claim 17, wherein the aggregate particles wherein the nanoparticulate drug particles have an effective average particle size of less than about 400 nm.

22. The method of claim 16 wherein said disease or condition comprises asthma.

23. The method of claim 16, wherein said disease or condition comprises COPD.

* * * * *